United States Patent
Zhu et al.

(10) Patent No.: US 10,066,272 B2
(45) Date of Patent: Sep. 4, 2018

(54) HUMAN HOMEOBOX GENE VENTX AND MACROPHAGE TERMINAL DIFFERENTIATION AND ACTIVATION, COMPOSITIONS AND METHODS THEREOF

(75) Inventors: Zhenglun Zhu, Allston, MA (US); Hong Gao, Allston, MA (US)

(73) Assignees: Zhenglun Zhu, Allston, MA (US); Hong Gao, Allston, MA (US)

( * ) Notice: Subject to any disclaimer, the term of this patent is extended or adjusted under 35 U.S.C. 154(b) by 832 days.

(21) Appl. No.: 14/119,220

(22) PCT Filed: Jun. 10, 2012

(86) PCT No.: PCT/US2012/041806
§ 371 (c)(1),
(2), (4) Date: Jun. 2, 2014

(87) PCT Pub. No.: WO2012/170979
PCT Pub. Date: Dec. 13, 2012

(65) Prior Publication Data
US 2014/0271682 A1    Sep. 18, 2014

Related U.S. Application Data

(60) Provisional application No. 61/495,849, filed on Jun. 10, 2011.

(51) Int. Cl.
| | |
|---|---|
| *C12Q 1/6897* | (2018.01) |
| *A61K 31/7088* | (2006.01) |
| *A61K 38/17* | (2006.01) |
| *C07K 14/00* | (2006.01) |
| *C07K 16/18* | (2006.01) |
| *C12N 15/113* | (2010.01) |

(52) U.S. Cl.
CPC ........ *C12Q 1/6897* (2013.01); *A61K 31/7088* (2013.01); *A61K 38/17* (2013.01); *C07K 14/00* (2013.01); *C07K 16/18* (2013.01); *C12N 15/113* (2013.01)

(58) Field of Classification Search
None
See application file for complete search history.

(56) References Cited

U.S. PATENT DOCUMENTS 7,994,126 B2 * 8/2011 Zhu ................. C07K 14/463
514/7.9

FOREIGN PATENT DOCUMENTS

| WO | WO 2007101063 A2 * | 9/2007 | ........... C07K 14/463 |
| WO | WO 2011008947 A2 * | 1/2011 | ......... A61K 31/7105 |

OTHER PUBLICATIONS

Gao et al., Cancer Res. Jan. 1, 2010;70(1):202-11. doi: 10.1158/0008-5472.CAN-09-2668. Epub Dec. 22, 2009.*
Simon et al., Cell Notes, 2008, issue 21, pp. 23-26.*
Hernandez-Garcia et al., Plant Sci. Mar. 2014;217-218:109-19. doi: 10.1016/j.plantsci.2013.12.007. Epub Dec. 14, 2013.*
Lubliner et al., Nucleic Acids Res. Jun. 2013;41(11):5569-81. doi: 10.1093/nar/gkt256. Epub Apr. 17, 2013.*
Juven-Gershon et al., Curr Opin Cell Biol. Jun. 2008;20(3):253-9. doi: 10.1016/j.ceb.2008.03.003. Epub Apr. 22, 2008.*

* cited by examiner

*Primary Examiner* — Michael Szperka
(74) *Attorney, Agent, or Firm* — Cesari & McKenna, LLP

(57) ABSTRACT

The invention generally relates to human biology discoveries and therapeutic and diagnostic compositions and methods based thereon. More particularly, the invention relates to human homeobox gene VentX and its control of macrophage terminal differentiation and activation, and related therapeutic and diagnostic compositions and methods of use, in particular in connection with inflammatory diseases.

5 Claims, 28 Drawing Sheets
Specification includes a Sequence Listing.

A

B

C

D

C

D

E

F

A

B

C

D  E

A

B

C

A

B

A

B

A

B

A

|  | siGFP | siVentX |
|---|---|---|
| Adhesion | 86.3 ± 6.4% | 33.8 ± 4.9% |
| Morphology change | 67.8 ± 6.3% | 6.6 ± 2.4% |

B

A

B

A

B

Fig. 24 B *Continued:*
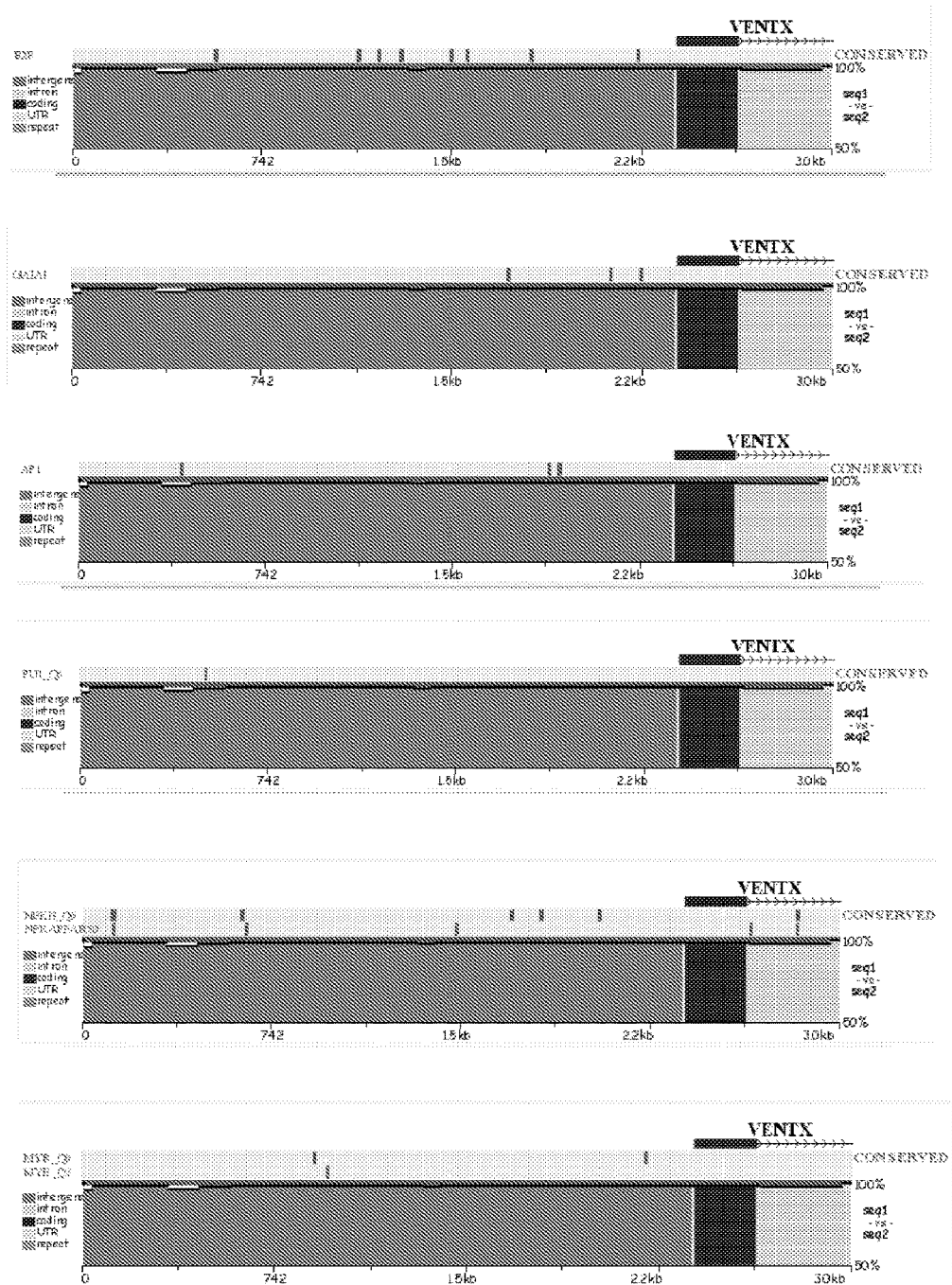

Human (Hom-1 polypeptide)

1
mrlssspprg pqqlssfgsv dwlsqsscsg pthtprpadf slgslpgpgq tsgareppqa 61
vsikeaagss nlpapertma glskepntlr aprvrtaftm eqvrtlegvf qhhqylsple 121
rkrlaremql sevqiktwfq nrrmkhkrqm qdpqlhspfs gslhappafy stssglangl 181
qllcpwapls gpqalmlppg sfwglcqvaq ealasagasc cgqplashpp tpgrpslgpa 241
lstgprglca mpqtgdaf Chimpanzee 1
mrlssspprg rqqlssfgsv dwlsqsscsg pthtprpadf slgslpgpgq tsgareppqa 61
vsikeaarss nlpapertva glskepntlr vprvrtaftm eqvrtlegvf qhhqylsple 121
rkrlaremql sevqiktwfq nrrmkhkrqm qdpqlhspfs gslpappafy spssglangl 181
qllcpwapls gpqalmlppg sfwglcqvaq ealasvgasc cgqplashpp tpgrptlgpa 241
lstgprglca mpqtgdaf Monkey 1
mrlssspprg qqqpssfgsv dwlsqsscsg ltpsprpadv spgslpgpgq isgareppqa 61
isikeavrrs alpspqpsmp glskepntlr gprvrtaftt eqvrtlegvf qhhqylsple 121
rkrlaremql sevqiktwfq nrrmkhkrqm qevppnspfl gslhvppafh spssglangl 181
qllcpwaplp gpqalmlppg sfwglcqveq ealastgasc crqplahhpp ttgsglpapgpa 241
lstgpwglca lpetgdaf

FIG. 25

HUMAN HOMEOBOX GENE VENTX AND MACROPHAGE TERMINAL DIFFERENTIATION AND ACTIVATION, COMPOSITIONS AND METHODS THEREOF

PRIORITY CLAIMS AND RELATED APPLICATIONS

This application is the national stage of International Application No. PCT/US2012/041806, filed Jun. 10, 2012, which claims the benefit of U.S. Provisional Application No. 61/495,849, filed Jun. 10, 2011, the entire content of which is expressly incorporated herein by reference.

TECHNICAL FIELDS OF THE INVENTION

The invention generally relates to human biology discoveries and therapeutic and diagnostic compositions and methods based thereon. More particularly, the invention relates to human homeobox gene VentX and its control of macrophage terminal differentiation and activation, and related therapeutic and diagnostic compositions and methods of use.

BACKGROUND OF THE INVENTION

Tissue macrophages are cells produced by the differentiation of monocytes in tissues in response to microenvironmental factors such as M-CSF (macrophage colony-stimulating factor), GM-CSF (granulocyte macrophage colony-stimulating factor), or IL3 during extravascularization. (Serbina, et al. 2008 *Annu Rev Immunol* 26:421-452.) Macrophages play critical roles in both innate and adaptive immunity in virtually all tissues. (Auffray, et al. 2009 *Annu Rev Immunol* 27:669-692; Martinez, et al. 2008 *Front Biosci* 13:453-461; Mosser, et al. 2008 *Nat Rev Immunol* 8:958-969.)

The process of monocyte to macrophage terminal differentiation remains a subject of extensive investigation in the contexts of immune defense against pathogen invasion, pathogenesis of autoimmune and inflammatory diseases, and carcinogenesis of hematopoietic and other malignancies. (Tenen 2003 *Nat Rev Cancer* 3:89-101.) Upon differentiation, the function of macrophages can be further activated by extracellular signals and displays diverse patterns depending upon the cytokines and microbial products present in the microenvironment.

Macrophage activation has been classified into a classical pathway and an alternative pathway. In response to Th1 cytokines, such as interferon γ (IFN-γ) and lipopolysaccharide (LPS), macrophages display a classical activation phenotype and produce mainly pro-inflammatory cytokines. The Jak/Stat and AP-1/NFκB signaling pathways have been shown to play critical roles in classical activation of macrophages. Alternatively, macrophages can be activated by Th2 cytokines, such as IL4 or IL13, and exhibit distinct functions with anti-inflammatory and tissue repair properties. (Martinez, et al. 2008 *Front Biosci* 13:453-461; Mosser, et al. 2008 *Nat Rev Immunol* 8:958-969; Gordon 2003 *Nat Rev Immunol* 3:23-35; Schroder, et al. 2006 *Immunobiology* 211:511-524.)

The common myeloid progenitor cells are the bone marrow precursors of monocytes and macrophages. It is generally accepted that monocyte and macrophage development occurs by changes of transcriptional programs in a stepwise manner. (Friedman 2007 *Oncogene* 26:6816-6828; Friedman 2002 *Oncogene* 21:3377-3390; Valledor, et al. 1998 *J Leukoc Biol* 63:405-417; Tenen, et al. 1997 *Blood* 90:489-519.) Genetic studies with knockout mice have revealed the important roles of transcription factors such as PU.1 and C/EBPα in monocyte/macrophage lineage commitment. (Yeamans, et al. 2007 *Blood* 110:3136-3142; Scott, et al. 1994 *Science* 265:1573-1577; McKercher, et al. 1996 *Embo J* 15:5647-5658.)

Recently, global transcriptome analysis revealed profound changes in gene expression during monocyte to macrophage terminal differentiation. (Liu, et al. 2008 *Immunol Lett* 117:70-80; Martinez, et al. 2006 *J Immunol* 177:7303-7311.) Previous studies on human monocyte to macrophage differentiation have mainly relied on myeloid progenitor cell lines like U937 and THP-1. (Lu, et al. 2001 *J Biol Chem* 276:45491-45496; Chang, et al. 2000 *Nat Immunol* 1:169-176; Liu, et al. 1996 *Genes Dev* 10:142-153.) The key transcriptional mechanism controlling primary human monocyte to macrophage differentiation remains poorly defined.

Developmental modeling is informative in defining genes and pathways involved in host defense and immune regulation. Using methods of reverse genetics, it was recently demonstrated that VentX, a human homologue of the Xenopus homeobox transcriptional factor Xom, is a LEF/TCF-associated Wnt repressor and a putative tumor suppressor. (Gao, et al. 2010 *Cancer Res* 70:202-211; Gao, et al. 2007 *Cell Res* 17:345-356; U.S. Pat. No. 7,994,126, expressly incorporated herein by reference for all purposes; WO/2011/00894, PCT/US2010/042126, expressly incorporated herein by reference for all purposes.) Also shown was that VentX trans-activates p53/p21 and $p16^{ink4a}$/Rb pathways to regulate senescence in tumor cells. (Wu, et al. 2011 *J Biol Chem* 286:12693-12701) VentX is predominantly expressed in hematopoietic cells and highly conserved in primates. However, researches have failed to identify the murine homologue of VentX in the current mouse genome database (20, 23, 24). (Gao, et al. 2010 *Cancer Res* 70:202-211; Ku, et al. 2006 *J Biol Chem* 281:5277-5287; Rawat, et al. 2010 *Proc Natl Acad Sci USA* 107:16946-16951.)

Therefore, a continued need exists for better understanding of the role of VentX, in particular in relation to microphage differentiation and activation, and therapeutic and/or diagnostic applications based therefrom.

SUMMARY OF THE INVENTION

The invention is based, in part, on the discovery that VentX plays an essential role in human primary monocyte to macrophage terminal differentiation and is required for optimal pro-inflammatory response during macrophage classical activation. For instance, the expression level of VentX correlates positively with the expression levels of several pro-inflammatory cytokines, indicating a role for VentX in the pathogenesis of inflammatory diseases.

In one aspect, the invention generally relates to a method for treating an inflammatory disease, comprising administering to a subject in need thereof a therapeutically effective amount of a composition comprising an biological or chemical agent that exerts a modulating effect of human homeobox gene VentX.

In another aspect, the invention generally relates to a pharmaceutical composition comprising an biological or chemical agent that exerts a modulating effect of human homeobox gene VentX.

In yet another aspect, the invention generally relates to a method for identifying a compound which regulates the VentX expression. The method includes: (a) providing a cell comprising a polynuceotide comprising VentX promoter; (b)

contacting the cell with a candidate compound; and (c) measuring the activity of VentX expression. In certain preferred embodiments, the VentX promoter sequence is of 2.8 KB, cloned with the primers: 5'-CAGCCGAGTCT-CACTCTGTC-3' (SEQ ID NO:1) and 5'-CAAAGCTGGA-GAGCTGCTGC-3' (SEQ ID NO:2), wherein the promoter sequence is placed in front of a luciferase gene to create a construct for a promoter-luciferase assay.

BRIEF DESCRIPTION OF THE DRAWINGS

FIG. 25 shows certain sequences of the invention. The sequences listed are a human Hom-1 polypeptide (SEQ ID NO: 110), a chimpanzee homolog (SEQ ID NO: 111), and a monkey homolog (SEQ ID NO: 112).

DEFINITIONS

Figure 1:
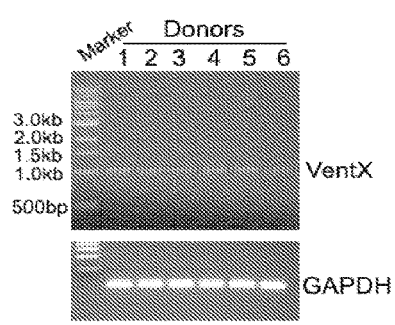
FIG. 1 shows exemplary Up-regulation of VentX expression during monocytes to macrophages differentiation. (A) VentX expression in circulating monocytes. Monocytes were magnetically isolated by anti-CD14 beads from peripheral blood of healthy adult donors. Total RNA was extracted and RT-PCR analysis of VentX mRNA level was conducted as described in Materials and Methods. (B) VentX expression during monocyte to macrophage differentiation in vitro. Monocytes were cultured in the presence of M-CSF (M), GM-CSF (GM) or IL3 for indicated days or in the absence of cytokines for 3 days. Upper panel, VentX mRNA levels were determined by RT-PCR; lower panel, VentX protein levels were determined by western blot analysis, using VentX specific antibodies. VentX expression in freshly isolated monocytes was used as baseline control (Day 0). (C) Induction of VentX promoter activity by indicated cytokines. Freshly isolated monocytes were electroporated with pGL3-VentX-promoter luciferase reporter construct or a control empty pGL3 luciferase reporter. Twenty-four hours post-electroporation, cells were treated with indicated cytokines for additional 24 hours. Cell lysates were then obtained and luciferase activities measured. Data represent mean+SD of triplicates of one representative experiment. (D) Time course of VentX expression during in vitro induction of monocytes differentiation into macrophages. Monocytes were subjected to M-CSF treatment in vitro for indicated time. The VentX mRNA levels were determined by quantitative PCR for up to 7 days.
Figure 1:
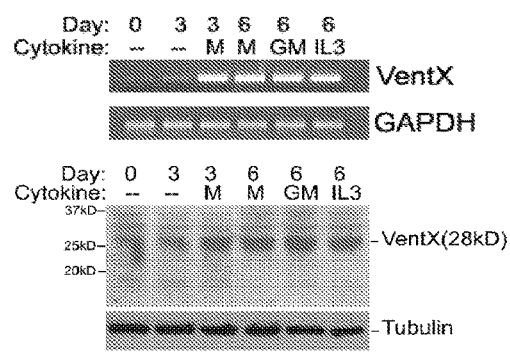
Figure 1:
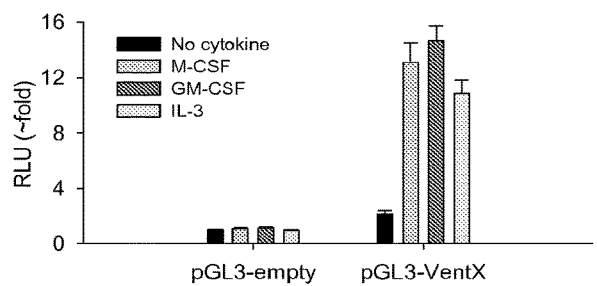
Figure 1:
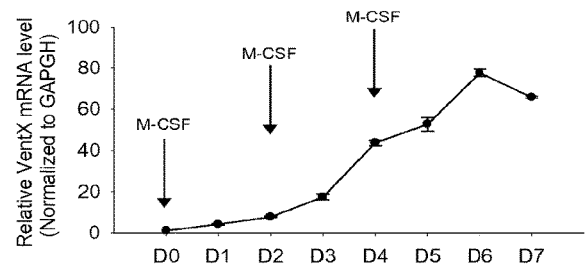

The definitions below are provided as summaries of concepts that are commonly understood by one of ordinary skill in the relevant art and are provided for the purposes of understanding of the subject matter disclosed herein. The definitions are not meant to be limitations of the invention or claims herein.

As used herein, the term "antibody" refers to molecules which are capable of binding an epitope or antigenic determinant. The term is meant to include whole antibodies and antigen-binding fragments thereof, including single-chain antibodies. The antibodies can be from any animal origin. Preferably, the antibodies are mammalian, e.g., human, murine, rabbit, goat, guinea pig, camel, horse and the like, or other suitable animals. Antibodies may recognize polypeptide or polynucleotide antigens. The term includes active fragments, including for example, an antigen binding fragment of an immunoglobulin, a variable and/or constant region of a heavy chain, a variable and/or constant region of a light chain, a complementarity determining region (cdr), and a framework region. The terms include polyclonal and monoclonal antibody preparations, as well as preparations including hybrid antibodies, altered antibodies, chimeric antibodies, hybrid antibody molecules, F(ab)$_2$ and F(ab) fragments; Fv molecules (for example, noncovalent heterodimers), dimeric and trimeric antibody fragment constructs; minibodies, humanized antibody molecules, and any functional fragments obtained from such molecules, wherein such fragments retain specific binding. The use of the singular terms "a" or "an" or "the" antibody are not meant to be limited to a single antibody when it is clear that more than one antibody is present in the composition or preparation. In addition, unless indicated otherwise, the singular term for "antibody" may include a collection of antibodies that are not necessarily heterogenous in their structures or specificities.

As used herein, the term "humanized" antibodies refer to a molecule having an antigen binding site that is substantially derived from an immunoglobulin from a non-human species and the remaining immunoglobulin structure of the molecule based upon the structure and/or sequence of a human immunoglobulin. The antigen binding site may comprise either complete variable domains fused onto constant domains or only the complementarity determining regions (CDRs) grafted onto appropriate framework regions in the variable domains. Antigen binding sites may be wild type or modified by one or more amino acid substitutions, e.g., modified to resemble human immunoglobulin more closely. Some forms of humanized antibodies preserve all CDR sequences (e.g., a humanized mouse antibody which contains all six CDRs from the mouse antibodies). Other forms of humanized antibodies have one or more CDRs (one, two, three, four, five, six) that are altered with respect to the original antibody.

The term "binds specifically," in the context of antibody binding, refers to high avidity and/or high affinity binding of an antibody to a specific epitope. Hence, an antibody that binds specifically to one epitope (a "first epitope") and not to another (a "second epitope") is a "specific antibody." An antibody specific to a first epitope may cross react with and bind to a second epitope if the two epitopes share homology or other similarity. The term "binds specifically," in the context of a polynucleotide, refers to hybridization under stringent conditions. Conditions that increase stringency of both DNA/DNA and DNA/RNA hybridization reactions are widely known and published in the art (Curr. Prot. Molec. Biol., John Wiley & Sons (2001)).

As used herein, the term "antigen" refers to a molecule capable of being bound by an antibody. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a Th cell epitope and is given in adjuvant. An antigen can have one or more epitopes (B- and/or T-cell epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens.

As used herein, the term "epitope" refers to basic element or smallest unit of recognition by an individual antibody or T-cell receptor, and thus the particular domain, region or molecular structure to which said antibody or T-cell receptor binds. An antigen may consist of numerous epitopes while a hapten, typically, may possess few epitopes.

As used herein, the term "nucleic acid molecule," "nucleotide," "oligonucleotide," "polynucleotide," and "nucleic acid" are used interchangeably herein to refer to polymeric forms of nucleotides of any length. They can include both double- and single-stranded sequences and include, but are not limited to, cDNA from viral, prokaryotic, and eukaryotic sources; mRNA; genomic DNA sequences from viral (e.g., DNA viruses and retroviruses) or prokaryotic sources; RNAi; cRNA; antisense molecules; ribozymes; and synthetic DNA sequences. The term also captures sequences that include any of the known base analogs of DNA and RNA.

As used herein, a "complementary" nucleotide sequence acid molecule is a one that is comprised of its base pair complements. Deoxyribonucleotides with the base adenine are complementary to those with the base thymidine, and deoxyribonucleotides with the base thymidine are complementary to those with the base adenine. Deoxyribonucleotides with the base cytosine are complementary to those with the base guanine, and deoxyribonucleotides with the base guanine are complementary to those with the base cytosine. Ribonucleotides with the base adenine are complementary to those with the base uracil, and deoxyribonucleotides with the base uracil are complementary to those with the base adenine. Ribonucleotides with the base cytosine are complementary to those with the base guanine, and deoxyribonucleotides with the base guanine are complementary to those with the base cytosine.

As used herein, the term "promoter" refers to a DNA regulatory region capable of binding RNA polymerase in a mammalian cell and initiating transcription of a downstream (3' direction) coding sequence operably linked thereto. For purposes of the present invention, a promoter sequence includes the minimum number of bases or elements necessary to initiate transcription of a gene of interest at levels detectable above background. Within the promoter sequence may be a transcription initiation site, as well as protein binding domains (consensus sequences) responsible for the binding of RNA polymerase. Eukaryotic promoters will often, but not always, contain "TATA" boxes and "CAT" boxes. Promoters include those that are naturally contiguous to a nucleic acid molecule and those that are not naturally contiguous to a nucleic acid molecule. Additionally, the term "promoter" includes inducible promoters, conditionally active promoters such as a cre-lox promoter, constitutive promoters, and tissue specific promoters.

As used herein, the term "transfected" means possessing introduced DNA or RNA, with or without the use of any accompanying facilitating agents such as lipofectamine. Methods for transfection that are known in the art include calcium phosphate transfection, DEAE dextran transfection, protoplast fusion, electroporation, and lipofection.

As used herein, the term "expression of a nucleic acid molecule" refers to the conversion of the information contained in the nucleic acid molecule into a gene product. The gene product can be the direct transcriptional product of a gene (e.g., mRNA, tRNA, rRNA, antisense RNA, ribozyme, structural RNA, or any other type of RNA) or a peptide or polypeptide produced by translation of an mRNA. Gene products also include RNAs that are modified by processes such as capping, polyadenylation, methylation, and editing; and proteins modified by, for example, methylation, acetylation, phosphorylation, ubiquitination, ADP-ribosylation, myristilation, and glycosylation.

As used herein, the term "host cell" refers to an individual cell or a cell culture that can be or has been a recipient of any recombinant vector(s) or isolated polynucleotide(s). Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell that comprises a recombinant vector of the invention may be called a "recombinant host cell."

As used herein, the term an "isolated" or "substantially isolated" molecule (such as a polypeptide or polynucleotide) is one that has been manipulated to exist in a higher concentration than in nature or has been removed from its native environment. For example, a subject antibody is isolated, purified, substantially isolated, or substantially purified when at least 10%, or 20%, or 40%, or 50%, or 70%, or 90% of non-subject-antibody materials with which it is associated in nature have been removed. For example, a polynucleotide or a polypeptide naturally present in a living animal is not "isolated," but the same polynucleotide or polypeptide separated from the coexisting materials of its natural state is "isolated." Further, recombinant DNA molecules contained in a vector are considered isolated for the purposes of the present invention. Isolated RNA molecules include in vivo or in vitro RNA replication products of DNA and RNA molecules. Isolated nucleic acid molecules further include synthetically produced molecules. Additionally, vector molecules contained in recombinant host cells are also isolated. Thus, not all "isolated" molecules need be "purified."

As used herein, the term "purified" when used in reference to a molecule, it means that the concentration of the molecule being purified has been increased relative to molecules associated with it in its natural environment, or environment in which it was produced, found or synthesized. Naturally associated molecules include proteins, nucleic acids, lipids and sugars but generally do not include water, buffers, and reagents added to maintain the integrity or facilitate the purification of the molecule being purified. According to this definition, a substance may be 5% or more, 10% or more, 20% or more, 30% or more, 40% or more, 50% or more, 60% or more, 70% or more, 80% or more, 90% or more, 95% or more, 98% or more, 99% or more, or 100% pure when considered relative to its contaminants.

As used herein, the term "biologically active" entity, or an entity having "biological activity," is one having structural, regulatory, or biochemical functions of a naturally occurring molecule or any function related to or associated with a metabolic or physiological process. Biologically active polynucleotide fragments are those exhibiting activity similar, but not necessarily identical, to an activity of a polynucleotide of the present invention. The biological activity can include an improved desired activity, or a decreased undesirable activity. For example, an entity demonstrates biological activity when it participates in a molecular interaction with another molecule, such as hybridization, when it has therapeutic value in alleviating a disease condition, when it has prophylactic value in inducing an immune response, when it has diagnostic and/or prognostic value in determining the presence of a molecule, such as a biologically active fragment of a polynucleotide that can, for example, be detected as unique for the polynucleotide molecule, or that can be used as a primer in a polymerase chain reaction. A biologically active polypeptide or fragment thereof includes one that can participate in a biological reaction.

As used herein, the terms "subject," "individual," and "patient" are used interchangeably herein to refer to a living animal, including a human and a non-human animal. The subject may, for example, be an organism possessing immune cells capable of responding to antigenic stimulation, and stimulatory and inhibitory signal transduction through cell surface receptor binding. The subject may be a mammal, such as a human or non-human mammal, for example, dogs, cats, pigs, cows, sheep, goats, horses, rats, and mice. The term "subject" does not preclude individuals that are entirely normal with respect to a disease, or normal in all respects.

As used herein, a "patient sample" is any biological specimen derived from a patient. The term includes, but is not limited to, biological fluids such as blood, serum, plasma, urine, cerebrospinal fluid, tears, saliva, lymph, dialysis fluid, lavage fluid, semen, and other liquid samples, as well as cell and tissues of biological origin. The term also includes cells or cells derived therefrom and the progeny thereof, including cells in culture, cell supernatants, and cell lysates. It further includes organ or tissue culture-derived fluids, tissue biopsy samples, tumor biopsy samples, stool samples, and fluids extracted from physiological tissues, as well as cells dissociated from solid tissues, tissue sections, and cell lysates. This definition encompasses samples that have been manipulated in any way after their procurement, such as by treatment with reagents, solubilization, or enrichment for certain components, such as polynucleotides or polypeptides. Also included in the term are derivatives and fractions of patient samples. A patient sample may be used in a diagnostic, prognostic, or other monitoring assay.

As used herein, the term "modulate" refers to the production, either directly or indirectly, of an increase or a decrease, a stimulation, inhibition, interference, or blockage in a measured activity when compared to a suitable control. A "modulator" of a polypeptide or polynucleotide or an "agent" are terms used interchangeably herein to refer to a substance that affects, for example, increases, decreases, stimulates, inhibits, interferes with, or blocks a measured activity of the polypeptide or polynucleotide, when compared to a suitable control.

As used herein, the terms "disease" or "disorder" refer to a pathological condition, for example, one that can be identified by symptoms or other identifying factors as diverging from a healthy or a normal state. The term "disease" includes disorders, syndromes, conditions, and injuries. Diseases include, but are not limited to, proliferative, inflammatory, immune, metabolic, infectious, and ischemic diseases.

As used herein, the term "inflammatory condition(s)" refers to the group of conditions including, rheumatoid arthritis, osteoarthritis, juvenile idiopathic arthritis, psoriasis, allergic airway disease (e.g., asthma, rhinitis), inflammatory bowel diseases (e.g., Crohn's disease, colitis), endotoxin-driven disease states (e.g., complications after bypass surgery or chronic endotoxin states contributing to e.g. chronic cardiac failure), and related diseases involving cartilage, such as that of the joints. Partcicularly the term refers to rheumatoid arthritis, osteoarthritis, allergic airway disease (e.g., asthma) and inflammatory bowel diseases.

As used herein, the term "autoimmune disease(s)" refers to the group of diseases including obstructive airways disease, including conditions such as COPD, asthma (e.g., intrinsic asthma, extrinsic asthma, dust asthma, infantily asthma) particularly chronic or inveterate asthma (for example late asthma and airway hyperreponsiveness), bronchitis, including bronchial asthma, systemic lupus erythematosus (SLE), multiple sclerosis, type I diabetes mellitus and complications associated therewith, atopic eczema (atopic dermatitis), contact dermatitis and further eczematous dermatitis, inflammatory bowel disease (e.g., Crohn's disease and ulcerative colitis), atherosclerosis and amyotrophic lateral sclerosis. Particularly the term refers to COPD, asthma, systemic lupus erythematosis, type I diabetes mellitus and inflammatory bowel disease.

As used herein the term "proliferative disease(s)" refers to conditions such as cancer (e.g., uterine leiomyosarcoma or prostate cancer), myeloproliferative disorders (e.g., polycythemia vera, essential thrombocytosis and myelofibrosis), leukemia (e.g., acute myeloid leukaemia and acute lymphoblastic leukemia), multiple myeloma, psoriasis, restenosis, sclerodermitis or fibrosis. In particular the term refers to cancer, leukemia, multiple myeloma and psoriasis.

As used herein, the terms "cancer" and "cancerous" refer to or describe the physiological condition in mammals that is typically characterized by unregulated cell growth. Examples of cancer include but are not limited to, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer.

As used herein, the term "tumor" refers to any malignant or neoplastic cell.

As used herein, the term "treatment" covers either prophylactic and/or therapeutic treatments including any administration or application of remedies for disease in a mammal, including a human, and includes inhibiting the disease. It includes arresting disease development and relieving the disease, such as by causing regression or restoring or repairing a lost, missing, or defective function, or stimulating an inefficient process. As used herein, the term "preventing" includes providing prophylaxis with respect to the occurrence or recurrence of a disease in a subject that may be predisposed to the disease but has not yet been diagnosed with the disease. Treatment and prophylaxis can be administered to an organism, including a human, or to a cell in vivo, in vitro, or ex vivo, and the cell subsequently administered the subject.

As used herein, the term "effective amount" refers to an amount necessary or sufficient to realize a desired biologic effect. An effective amount of the composition would be the amount that achieves this selected result, and such an amount could be determined as a matter of routine by a person skilled in the art. For example, an effective amount for treating an immune system deficiency could be that amount necessary to cause activation of the immune system, resulting in the development of an antigen specific immune response upon exposure to antigen. The term is also synonymous with "sufficient amount." The effective amount for any particular application can vary depending on such factors as the disease or condition being treated, the particular composition being administered, the size of the subject, and/or the severity of the disease or condition. One of ordinary skill in the art can empirically determine the effective amount of a particular composition of the present invention without necessitating undue experimentation.

As used herein, the term "carrier" refers to a solid, semisolid or liquid filler, diluent, encapsulating material, formulation auxiliary, or excipient of any conventional type. A "pharmaceutically acceptable carrier" refers to a non-toxic "carrier." A pharmaceutically acceptable carrier is non-toxic to recipients at the dosages and concentrations employed and is compatible with other ingredients of the formulation. Pharmaceutically acceptable carriers can be, for example, vehicles, adjuvants, or diluents.

As used herein, the terms "polypeptide" and "protein" are used interchangeably to refer to a polymer of amino acid residues, and are not limited to a minimum length. Thus, peptides, oligopeptides, dimers, multimers, and the like, are included within the definition. Both full-length proteins and fragments thereof are encompassed by the definition. The terms also include post-expression modifications of the polypeptide, for example, glycosylation, acetylation, phosphorylation, and the like. Furthermore, a "polypeptide" may refer to a protein which includes modifications, such as deletions, additions, and substitutions (generally conservative in nature), to the native sequence, as long as the protein maintains the desired activity. These modifications may be deliberate or may be accidental.

As used herein, the term "receptor" refers to proteins or glycoproteins or fragments thereof capable of interacting with another molecule, called the ligand. The ligand may belong to any class of biochemical or chemical compounds. The ligand is usually an extracellular molecule which, upon binding to the receptor, usually initiates a cellular response, such as initiation of a signal transduction pathway. The receptor need not necessarily be a membrane-bound protein.

As used herein, the term "recombinant," with respect to a nucleic acid molecule, means a polynucleotide of genomic, cDNA, viral, semisynthetic, and/or synthetic origin which, by virtue of its origin or manipulation, is not associated with all or a portion of the polynucleotide with which it is associated in nature. The term "recombinant", as used with respect to a protein or polypeptide, means a polypeptide produced by expression of a recombinant polynucleotide. The term "recombinant" as used with respect to a host cell means a host cell into which a recombinant polynucleotide has been introduced.

As used herein, the phrase "recombinant virus" refers to a virus that is genetically modified by the hand of man. The phrase covers any virus known in the art.

As used herein, the term "vector" refers to an agent (e.g., a plasmid or virus) used to transmit genetic material to a host cell or organism. A vector may be composed of either DNA or RNA.

As used herein, the term "interfering RNA" or "RNAi" or "interfering RNA sequence" refers to double-stranded RNA (i.e., duplex RNA) that is capable of reducing or inhibiting expression of a target gene (i.e., by mediating the degradation of mRNAs which are complementary to the sequence of the interfering RNA) when the interfering RNA is in the same cell as the target gene. Interfering RNA thus refers to the double-stranded RNA formed by two complementary strands or by a single, self-complementary strand. Interfering RNA may have substantial or complete identity to the target gene or may comprise a region of mismatch (i.e., a mismatch motif). The sequence of the interfering RNA can correspond to the full length target gene, or a subsequence thereof. Interfering RNA includes "small-interfering RNA" or "siRNA," e.g., interfering RNA of about 15-60, 15-50, or 15-40 (duplex) nucleotides in length, more typically about 15-30, 15-25, or 19-25 (duplex) nucleotides in length).

As used herein, the term "sample" refers to a sample from a human, animal, or to a research sample, e.g., a cell, tissue, organ, fluid, gas, aerosol, slurry, colloid, or coagulated material. The "sample" may be tested in vivo, e.g., without removal from the human or animal, or it may be tested in vitro. The sample may be tested after processing, e.g., by histological methods. "Sample" also refers, e.g., to a cell comprising a fluid or tissue sample or a cell separated from a fluid or tissue sample. "Sample" may also refer to a cell, tissue, organ, or fluid that is freshly taken from a human or animal, or to a cell, tissue, organ, or fluid that is processed or stored.

DETAILED DESCRIPTION OF THE INVENTION

The invention is based, in part, on the discovery that VentX plays an essential role in human primary monocyte to macrophage terminal differentiation and is required for optimal pro-inflammatory response during macrophage classical activation. For instance, the expression level of VentX correlates positively with the expression levels of several pro-inflammatory cytokines, indicating a role for VentX in the pathogenesis of inflammatory diseases.

VentX Regulates Monocyte to Macrophage Terminal Differentiation

The molecular mechanisms underlying monocyte/macrophage development have been extensively investigated for their broad implications in host defense, autoimmunity, inflammatory control, and tissue repair and regeneration (1, 3, 10, 53). (Auffray, et al. 2009 *Annu Rev Immunol* 27:669-692; Mosser, et al. 2008 *Nat Rev Immunol* 8:958-969; Valledor, et al. 1998 *J Leukoc Biol* 63:405-417; Gordon, et al. 2005 *Nat Rev Immunol* 5:953-964.) Monocytes/macrophages arise from pluripotent hematopoietic stem cells in the bone marrow through multiple stages of concerted expression of signaling molecules and transcriptional factors. (Friedman 2007 *Oncogene* 26:6816-6828; Valledor, et al. 1998 *J Leukoc Biol* 63:405-417; Tenen, et al. 1997 *Blood* 90:489-519.) Extensive genetic studies in knockout mice have identified several transcriptional factors that are important for specification of myeloid progenitor cells and subsequent monocyte/macrophage lineage commitment. (Feinberg, et al. 2007 *Embo J* 26:4138-4148.) In particular, the Ets family transcriptional factor PU.1 and C/EBP family member C/EBPα represent master regulators of myeloid lineage development. (Tenen, et al. 1997 *Blood* 90:489-519; Yeamans, et al. 2007 *Blood* 110:3136-3142; Scott, et al. 1994 *Science* 265:1573-1577; McKercher, et al. 1996 *Embo J* 15:5647-5658.)

Figure 2:
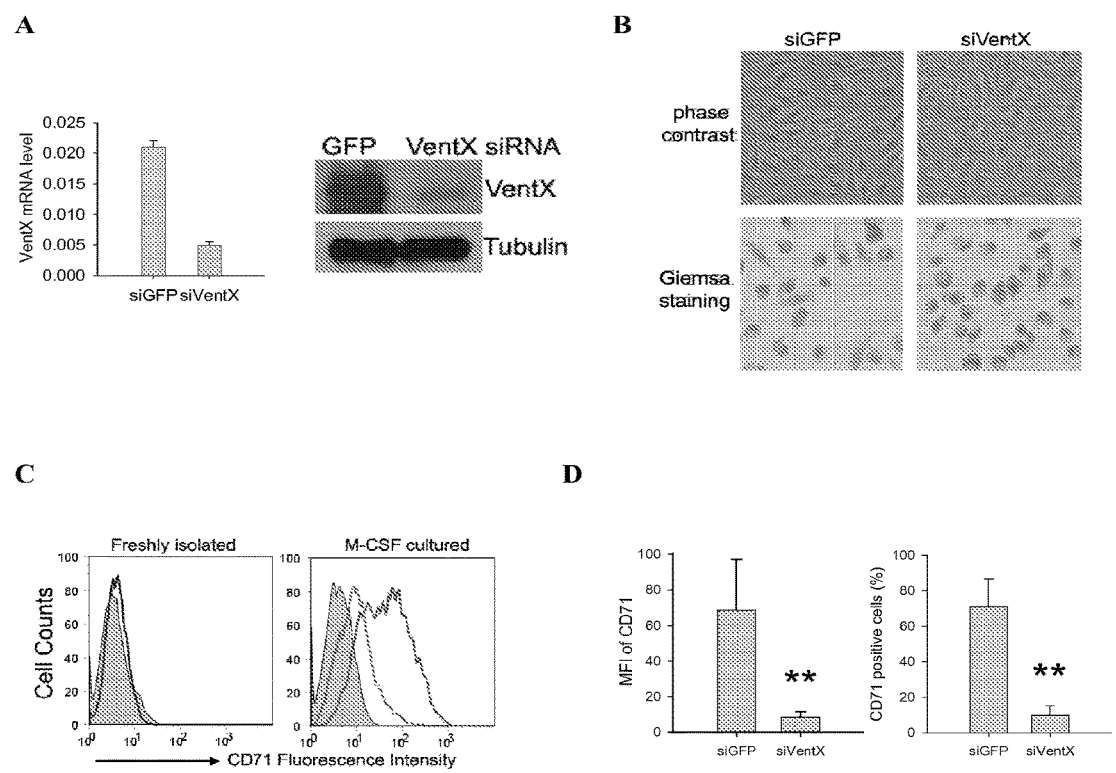
FIG. 2 shows that knockdown of VentX compromises the macrophage differentiation of primary monocytes. (A) knockdown of VentX expression in primary monocytes by RNA interference. Monocytes were transfected with siRNA against GFP or VentX through electroporation. VentX mRNA levels were determined by real time PCR at 3 days after transfection (left); VentX protein level was determined by western blotting at 4 days after transfection (right). (B) Effects of VentX knockdown on macrophage morphogenesis during M-CSF induced differentiation. Monocytes were transfected with either siGFP or siVentX and subsequently exposed to 100 ng/mL M-CSF. At 4 days post transfection, the morphology of macrophages was revealed by phase contrast microscopy (upper panel) and Wright-Giemsa staining (lower panel). Magnification of photographs, ×200. Note: a portion of cells lost their original morphology during Wright-Giemsa staining procedure. (C) Effects of VentX knockdown on macrophage surface expression of CD71. Left panel: CD71 expression was not detected on cell surface from freshly isolated monocytes; right panel: CD71 expression on M-CSF treated monocytes at 4 days after siRNA transfection. Filled blue histogram represents the isotope control staining; red histogram represents monocytes transfected with siGFP; green histogram represents monocytes transfected with siVentX. (D) Bar graphs show mean+SD of 6 different experiments in (C). Paired t test was used to reveal the statistical significance. **$p<0.01$.

Nevertheless, it is clear that monocyte/macrophage lineage commitment is distinct from differentiation of monocytes into mature macrophages; the latter is accompanied by marked changes in cell morphology and immune functions and requires a new set of expressed genes. (Liu, et al. 2008 *Immunol Lett* 117:70-80; Martinez, et al. 2006 *J Immunol* 177:7303-7311; Imhof, et al. 2004 *Nat Rev Immunol* 4:432-444; Gordon, et al. 2005 *Nat Rev Immunol* 5:953-964.) However, little is known about the transcriptional regulation of terminal monocyte to macrophage differentiation. The data suggest that VentX is a key regulator of this process. In the knockdown experiments, 50% to 70% of VentX suppression could be achieved with the siRNA approach, which resulted in a remarkable 80% reduction of CD71 expression (FIG. 2). Meanwhile, cells lost normal fibroblast-like morphology and showed weaker phagocytotic activity, indicating that VentX deficiency affects various aspects of macrophage differentiation and function. Moreover, consistent with the up-regulated expression of VentX during monocyte to macrophage differentiation, over-expression of VentX in primary monocytes was able to promote macrophagic differentiation (unpublished data). Further, it was shown that ectopic expression of VentX alone was sufficient to drive macrophagic differentiation of U937 cells. Although transcription factors, such as the BLIMP-1, IRF-7, PU.1, and NF-κB have been shown to be important for U937 differentiation, their specific involvement in primary human monocyte to macrophage differentiation was not defined. (Lu, et al. 2001 *J Biol Chem* 276:45491-45496; Chang, et al. 2000 *Nat Immunol* 1:169-176; Garcia, et al. 1999 *Exp Hematol* 27:353-364.) VentX is the first transcription factor both necessary and sufficient for human primary monocyte to macrophage differentiation. Interestingly, despite its prominent role in human monocyte to macrophage differentiation, people were unable to identify a murine homolog of VentX. Strikingly, the two genes that flank the VentX gene in the human genome (UTF1 and ADAM8) are syntenic in the mouse genome, however, there appears to be no VentX homologue in the mouse. (Rawat, et al. 2010 *Proc Natl Acad Sci USA* 107:16946-16951.)

Figure 24:
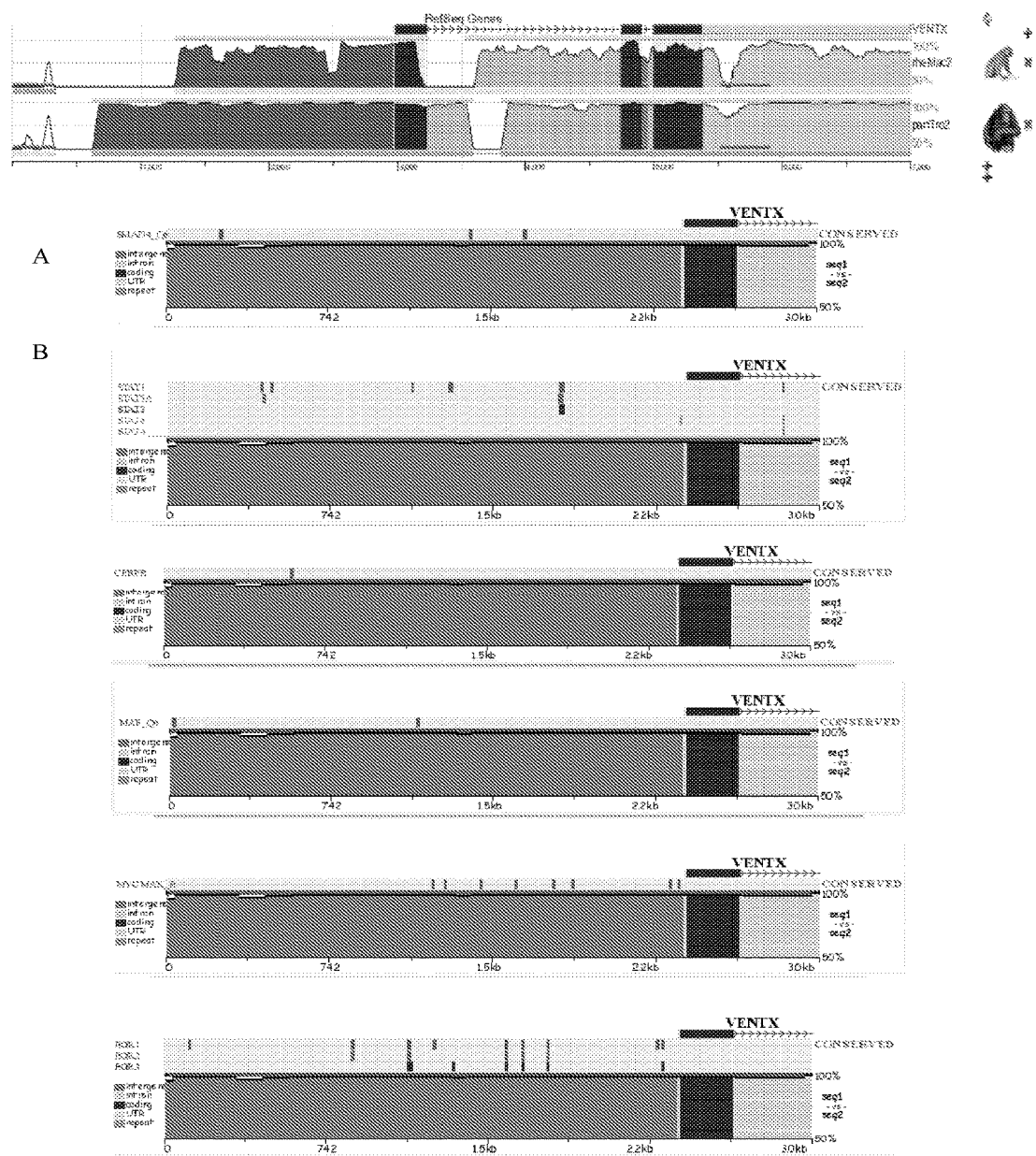
FIG. 24 shows exemplary ECR browser analysis of VentX loci among human, chimpanzee and rhesus monkey. (A) The VentX loci of human, chimpanzee (panTro2) and rhesus monkey (rheMac2) were analyzed by ECR browser (http://ecrbrowser.dcode.org). The human genomic sequence of chr10:134898423-134905423 (~7 Kb), which encompasses the VentX locus, was used as base genome. VentX gene is depicted as a horizontal blue line above the graph, with strand/transcriptional orientation indicated by arrow. Blue boxes along the line correspond to positions of coding exons, while yellow boxes correspond to UTRs. Peaks within the conservation profile that correspond to these exons are similarly colored within the plot. Peaks within the conservation profile that do not correspond to transcribed sequences are highlighted in red if they are intergenic or salmon if they lie within an intron. Regions colored in green correspond to transposable elements and simple repeats. The sequence of the base genome is represented on the horizontal axis, and the vertical position corresponds to the level of nucleotide identity in this alignment. (B) The promoter region of VentX loci (Shown in Red) was analyzed for conserved transcriptional factors binding sites from TRANSFAC professional V10.2 library.

Among the questions to be answered are the molecular mechanisms of VentX upregulation during monocyte to macrophage differentiation (FIG. 1). Promoter analysis with ECR browser found that VentX promoter region is highly conserved among primates (chimpanzee and rhesus monkey, FIG. 24A). Detailed analysis of VentX promoter revealed several evolutionarily conserved binding sites for transcriptional factors implicated in macrophage differentiation, such as C/EBP, Egr-1, AP1 and NFKB (FIG. 24B). (Friedman 2007 *Oncogene* 26:6816-6828.)

Mechanism of Regulation of Macrophage Differentiation by VentX

Figure 5:
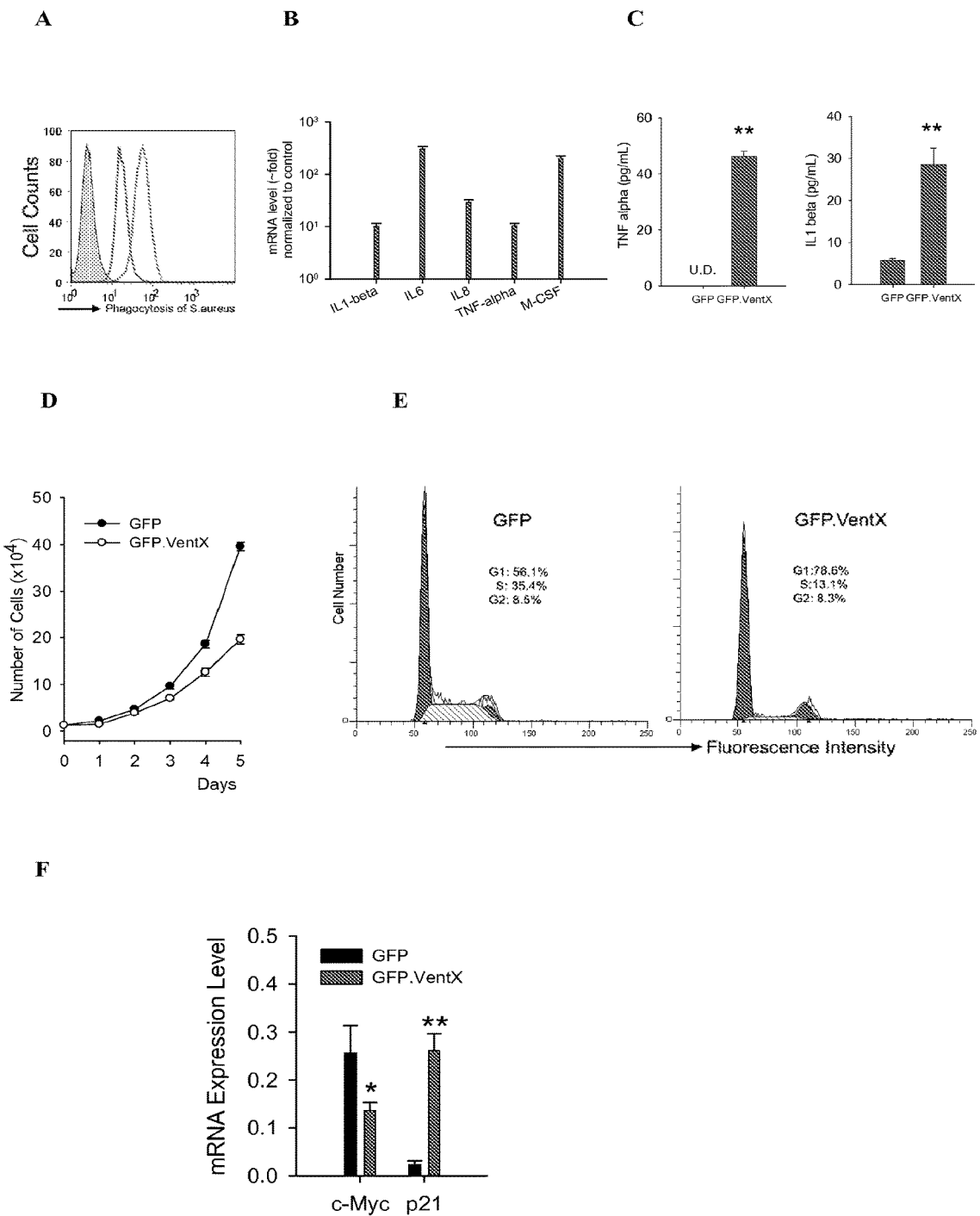
FIG. 5 shows that VentX promotes pro-inflammatory response and inhibits proliferation in U937 cells. U937 cell lines were treated as described in FIG. 4. (A) Phagocytosis of DOX-treated U937 cells at 37° C. Red histogram represent GFP expressing cells; green histogram represent GFP.VentX expressing cells. Filled blue histogram represents background staining of cells without undergoing phagocytosis. (B) Effects of VentX expression on the mRNA level of pro-inflammatory cytokines U937 cells were treated with 1 µg/mL LPS for 6 hours after 72 hours exposure to DOX. Real-time PCR was performed to determine mRNA levels of the indicated cytokines Data are presented as the fold of elevation and are mean+SD of triplicates from one representative experiment. (C) Secreted IL1-β and TNF-α from U937 cell culture supernatants were determined with ELISA kits. U.D. means undetectable. Data represent mean+SD of triplicates from one representative experiment. (D) Effects of VentX on growth of U937 cells. $2 \times 10^4$ cells were seeded in 6-well plates and cultured for 5 days in the presence of 1.0 µg/mL DOX. Cell numbers at indicated days were counted and plotted. (E) Cell cycle profiles of U937 cells expressing GFP or GFP.VentX after 3 days exposure to DOX. Cells were stained with propidium iodide and analyzed by FACS. (F) Effects of VentX on mRNA levels of c-Myc and p21 as determined by real time PCR. Data represent mean+SD of triplicates from one representative experiment.
Figure 6:
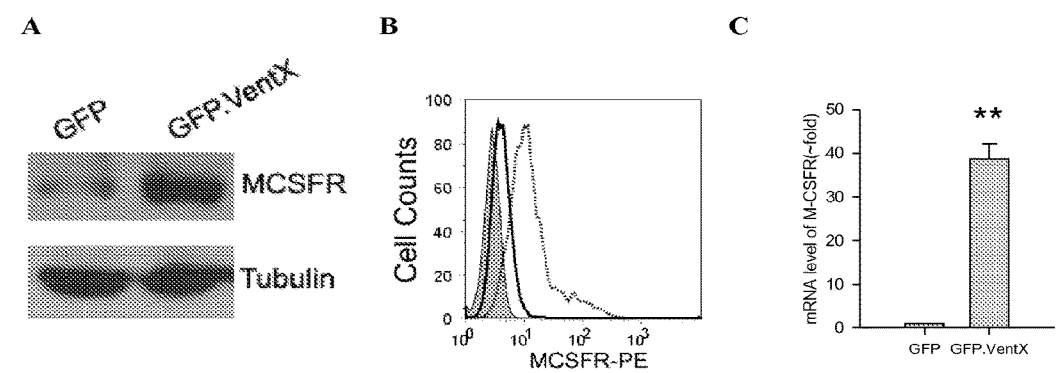
FIG. 6 shows that VentX trans-activates M-CSF receptor expression. (A-C) U937 cell lines expressing GFP or GFP.VentX under the control of tetracycline-inducible promoter were treated with 1.0 µg/mL DOX for 72 hours. (A) Western blotting analysis of M-CSF receptor (M-CSFR) protein levels from U937 cell lysates. Tubulin was used as a loading control. (B) Surface expression of M-CSFR was determined by FACS analysis. Filled gray histogram represents isotype control; solid line histogram represents cells expressing GFP; dotted line histogram represents cells expressing GFP.VentX. (C) M-CSFR mRNA levels were determined by real-time PCR. Data represent mean+SD of triplicates from one representative experiment. (D) VentX transactivation of M-CSFR promoter. pcDNA-VentX or pcDNA-control were co-transfected with wild type or mutant M-CSFR promoter luciferase reporter constructs into U937 cells. The effect of VentX on M-CSFR promoter transactivation was determined by luciferase activity. Data are mean+SD of triplicates from one representative experiment. (E) ChIP analysis of the interaction between VentX and the M-CSFR promoter, showing the association of VentX with M-CSFR promoter region but not with Cµ region in U937 cells. (F) Gel shift analysis showing the binding of VentX to the wild type M-CSFR promoter (wt) probe, but reduced binding to the mutant M-CSFR promoter (mut) probe.
Figure 6:
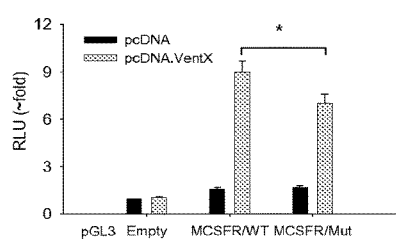
Figure 6:
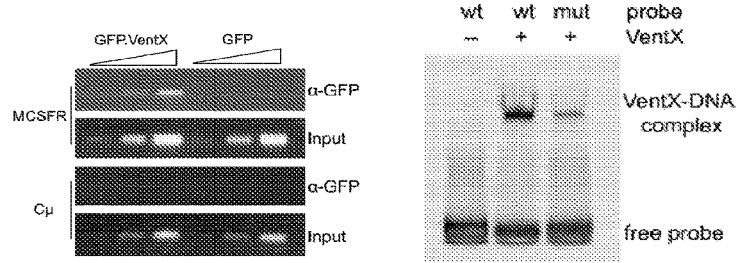
Figure 15:
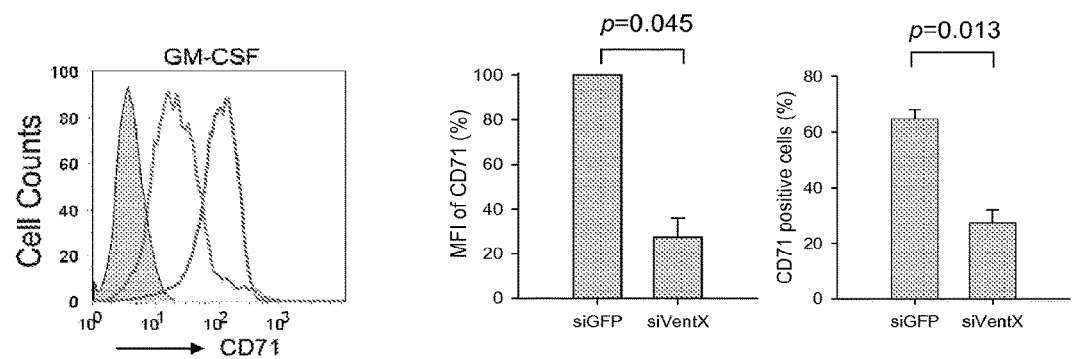
FIG. 15 shows that VentX is required for macrophage differentiation of primary monocytes in GM-CSF and IL3 cultures. Monocytes were transfected with either siGFP or siVentX and subsequently exposed to 100 ng/mL GM-CSF (A) or IL3 (B) to trigger macrophagic differentiation. Surface expression of CD71 was determined by FACS analysis at 4 days after siRNA transfection. Filled blue histogram represents the isotope control staining; red histogram: monocytes transfected with siGFP; green histogram: monocytes transfected with siVentX.
Figure 15:
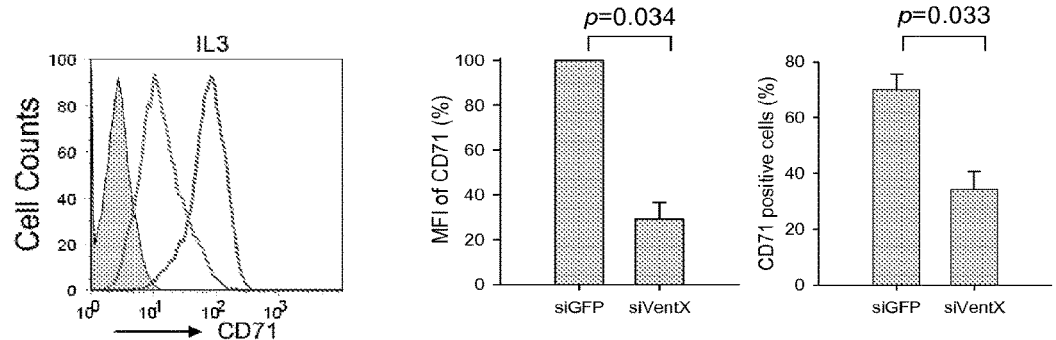

M-CSF receptor (M-CSFR, also called csflr) is an integral membrane tyrosine kinase encoded by the c-fms proto-oncogene. M-CSFR is expressed in monocytes/macrophages and their progenitors, and is obligatory for macrophage differentiation. (Bourette, et al. 2000 *Growth Factors* 17:155-166; Pixley, et al. 2004 *Trends Cell Biol* 14:628-638.) Several cytokines and transcription factors regulate macrophage differentiation via modulating expression of M-CSFR (37, 58, 59). (Shi, et al. 2004 *J Clin Invest* 114:408-418.) In FIG. 6, it was demonstrated that M-CSFR is a transcriptional target of VentX through various biochemical approaches. VentX binds to the HDB site of M-CSFR promoter and directly transactivates M-CSFR expression. When M-CSFR plasmid was supplemented into siVentX transfected monocytes, the macrophage differentiation defect was partially restored (FIG. 19), indicating that M-CSFR is a physiologically important target of VentX in macrophage differentiation. Interestingly, the promoter regions of human and murine M-CSFR genes show little conservation (analyzed by ECR browser, not shown). Therefore, transcriptional activation of M-CSFR by VentX is likely a unique pathway for human monocytes. Besides the M-CSFR pathway, the finding that ectopic expression of VentX alone is able to drive macrophage differentiation of U937 cells suggests the existence of other mechanisms underlying VentX induced macrophage differentiation, because M-CSF is not required for U937 differentiation. Previous studies have showed that downregulation of c-Myc and upregulation of p21 promote macrophage differentiation of U937 cells (9, 10, 18, 19, 60). (Friedman 2002 *Oncogene* 21:3377-3390; Valledor, et al. 1998 *J Leukoc Biol* 63:405-417; Chang, et al. 2000 *Nat Immunol* 1:169-176; Liu, et al. 1996 *Genes Dev* 10:142-153; Kramer, et al. 2002 *Br J Haematol* 117:727-734.) The data showed that c-Myc and p21 can be regulated by VentX in U937 cells (FIG. 5F). In addition, knockdown of VentX also down-regulated the expression of GM-CSF and IL3 receptors (unpublished data), which may explain the differentiation defects after GM-CSF and IL3 treatments (FIG. 15).

VentX Controls Macrophage Pro-Inflammatory Responses

Knockdown of VentX caused downregulation of multiple membrane receptors critical for innate and adaptive immunity, including Toll-like receptor 4, mannose receptor, Fcγ receptor CD64, co-stimulatory molecules CD40, CD80 and CD86, and adhesion molecules CD11b and CD11c. As a consequence, the profoundly phenotypic and functional changes were observed in VentX silenced monocytes/macrophages. Specifically, downregulation of TLR4, CD14, MR and CD64 may contribute to the impaired phagocytotic ability of monocyte/macrophage (61). Aberrant morphogenesis and adherence may relate to the downregulation of adhesion molecules CD11b and CD11c. (Imhof, et al. 2004 *Nat Rev Immunol* 4:432-444.) Downregulation of co-stimulatory molecules CD40, CD80 and CD86 on membrane may weaken the capability of macrophage to stimulate T cell proliferation (FIG. 8F). VentX also regulates the expression of Stat1 and AP-1 transcription factors, the essential components of the IFN-γ and LPS signaling pathways.

Figure 8:
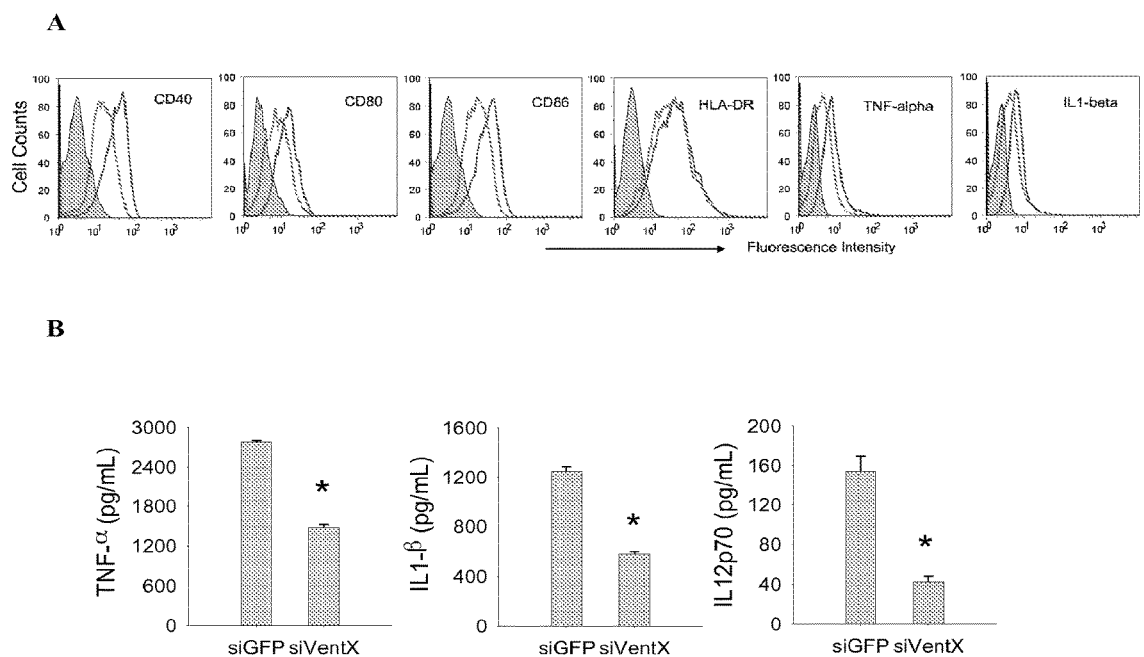
FIG. 8 shows that VentX expression is required for macrophage classical activation. Macrophages were generated through incubation of freshly isolated monocytes with 100 ng/mL M-CSF for 4 days. These macrophages were then transfected with siGFP or siVentX, respectively, and further cultured in RPMI 1640 medium for additional 3 days. Thereafter, cells were exposed to 1 µg/mL LPS plus 20 ng/mL γ-IFN for 6 hours. (A) Surface staining of CD40, CD80, CD86 and HLA-DR and intracellular staining of TNF-α and IL1-β were analyzed by flow cytometry. (B) Secreted TNF-α, IL1-β and IL12p70 from culture supernatants were determined with ELISA kits. (C) Reactive oxygen species (ROS) from siGFP or siVentX transfected macrophages were analyzed with fluorescence microscope (left) and flow cytometry (middle). Right panel: Bar graph shows mean+SD of three different flow cytometry experiments. (D) Nitrate level from siGFP and siVentX transfected macrophages. Data represent mean+SD of three different experiments. (E) Phagocytosis of siGFP and siVentX transfected macrophage. Red histogram represents transfection with siGFP; green histogram represents transfection with siVentX. Left panel: cells were incubated on ice; right panel: cells were incubated at 37° C. (F) Effects of VentX knockdown on mixed lymphocyte reaction. Irradiated macrophages that had been transfected with siGFP or siVentX were utilized to stimulate allogenic naïve CD4 T cells proliferation. The proliferation rates were represented by counts per minute (CPM). Results show mean+SD of triplicates of one representative experiment. Statistically significant difference ($p<0.05$) was observed when $4\times10^2$ or $2\times10^3$ cells were added.
Figure 8:
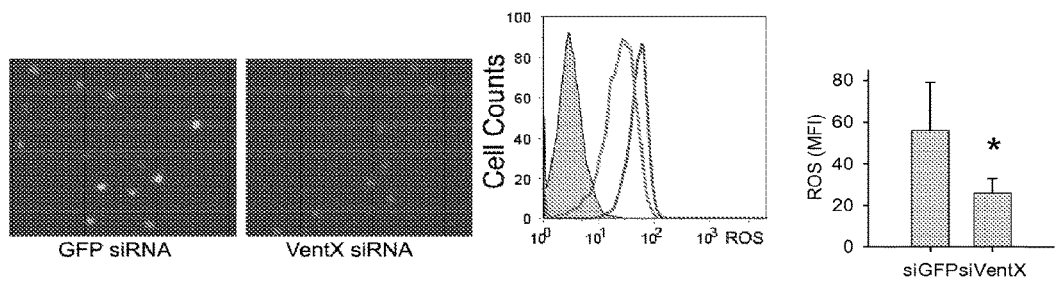
Figure 8:
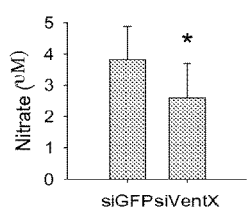
Figure 8:
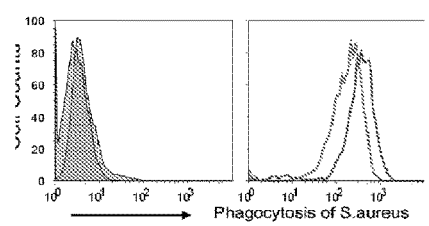
Figure 8:
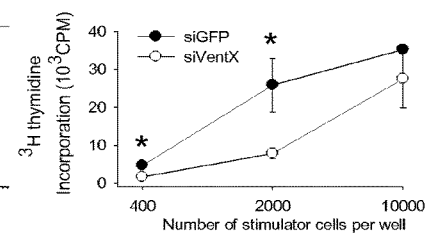

Consequently, knockdown of VentX rendered macrophages unable to mount optimal pro-inflammatory response upon classical activation (FIG. 8). In contrast, over-expression of VentX enhanced secretion of pro-inflammatory cytokines in U937 cells (FIG. 5B-C). In addition, other factors implicated in macrophage activation, such as HIF-1 and p300 co-activator complex, may also be involved in VentX-mediated inflammatory response. The study therefore indicates that VentX targets multiple pathways and plays critical roles in various aspects of monocyte/macrophage biology. The clinical implication of VentX in regulation of inflammatory response was suggested by the observation that expression levels of VentX and several pro-inflammatory cytokines correlate positively in patients with autoimmune diseases (SLE and RA). The pathogenesis of these diseases is multifactorial and involves abnormalities in both the innate and adaptive immunity. The increased expression of pro-inflammatory cytokines such as TNF-α and IL6 have been related to the induction of the diseases. (Pringe, et al. 2007 *Lupus* 16:587-592; Gualtierotti, et al. 2010 *Autoimmun Rev* 10:3-7.)

Thus, dysregulated expression of VentX in macrophages may play a role in the pathogenesis of autoimmune diseases. Moreover, it was found that expression of VentX could be down-regulated by immunosuppressive therapy in SLE/RA patients (FIG. 23), suggesting a potential role of VentX as a future therapeutic target and in clinical management of autoimmune and inflammatory disorders.

In one aspect, the invention generally relates to a method for treating an inflammatory disease, comprising administering to a subject in need thereof a therapeutically effective amount of a composition comprising an biological or chemical agent that exerts a modulating effect of human homeobox gene VentX.

In certain preferred embodiments, the modulating effect comprises an inhibiting effect.

In certain preferred embodiments, the biological or chemical agent is a polypeptide. For example, the biological or chemical agent may comprise a VentX mutant lacking the homeodomain as a blocking polypeptide. The biological or chemical agent comprises the VentX homeodomain without other activating domain as a blocking polypeptide.

In certain preferred embodiments, the polypeptide may be delivered into cells via a short delivery peptide.

In certain preferred embodiments, the biological or chemical agent is an antibody fragment.

In certain preferred embodiments, the biological or chemical agent is an oligonucleotide, for example, an RNAi.

In another aspect, the invention generally relates to a pharmaceutical composition comprising an biological or chemical agent that exerts a modulating effect of human homeobox gene VentX.

In certain preferred embodiments, the modulating effect comprises an inhibiting effect for treatment of inflammatory autoimmnune conditions In certain preferred embodiments, the modulating effect comprises that of an immunosuppressant selected from corticosteroid, 6-MP, methotraxate, cellcept and aziothropine.

In certain preferred embodiments, the modulating effect comprises an activating effect comprising that of chemotherapy agents selected from 5-FU, Retinoid acid and DOX.

In certain preferred embodiments, the biological or chemical agent is a polypeptide.

In certain preferred embodiments, the biological or chemical agent is an antibody.

In certain preferred embodiments, the biological or chemical agent is an oligonucleotide.

In another aspect, the invention generally relates to a method for identifying a compound which regulates the VentX expression. The method includes: (a) providing a cell comprising a polynuceotide comprising VentX promoter; (b) contacting the cell with a candidate compound; and (c) measuring the activity of VentX expression.

In certain preferred embodiments, the VentX promoter sequence is of 2.8 KB, cloned with the primers: 5'-CAGC-CGAGTCTCACTCTGTC-3' (SEQ ID NO:1) and 5'-CAAAGCTGGAGAGCTGCTGC-3' (SEQ ID NO:2), wherein the promoter sequence is placed in front of a luciferase gene to create a construct for a promoter-luciferase assay.

In certain preferred embodiments, the compound is a small molecule agent. In certain preferred embodiments, the compound is a polypeptide. In certain preferred embodiments, the compound is an oligonucleotide.

EXAMPLES

VentX Expression is Up-Regulated During Monocyte to Macrophage Differentiation

Tissue expression profiling showed that VentX is expressed in monocytes (20). To explore the potential role of VentX in monocyte to macrophage differentiation, VentX expression in peripheral blood monocytes was examined from six healthy donors by RT-PCR. It was found that VentX expression was relatively constant among different individuals (FIG. 1A). In comparison, VentX expression was up-regulated during monocyte to macrophage differentiation induced by cytokines such as M-CSF, GM-CSF and IL3 (FIG. 1B, upper panel). Using promoter luciferase assay, it was found that VentX promoter can be activated by the indicated cytokines (FIG. 1C), suggesting that VentX expression was transcriptionally regulated by the differentiation signals. The regulated expression of VentX was further demonstrated by western blotting analysis, using VentX specific antibody (FIG. 1B, lower panel). The significant upregulation of VentX expression was largely dependent on the addition of the cytokines. Nevertheless, a slight but discernable upregulation of VentX expression was also observed in the absence of inducing factors (FIG. 1B, lane 1 and 2), which may reflect adhesion induced spontaneous differentiation of monocytes. To quantitatively measure VentX expression during in vitro monocyte to macrophage differentiation, a time course experiment was performed with real time PCR analysis. As shown in FIG. 1D, VentX expression was rapidly induced during the first 4 days of cytokine treatment and remained at a high level throughout the 7 days of in vitro culture.

VentX is Required for Human Primary Monocyte to Macrophage Differentiation

Figure 3:
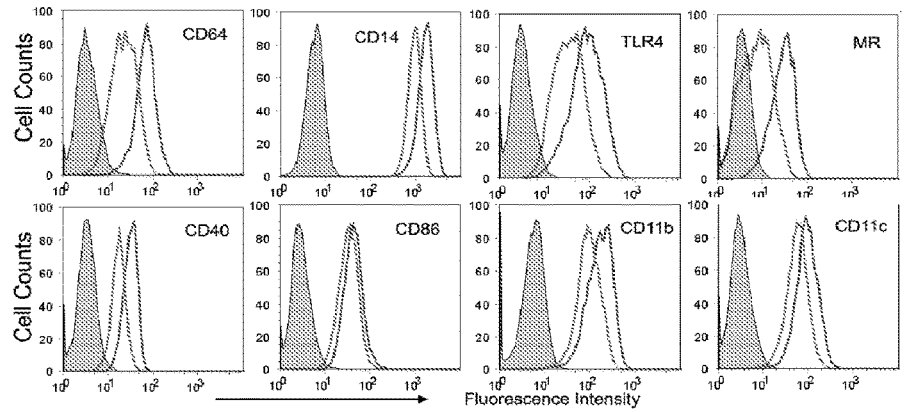
FIG. 3 shows exemplary effects of VentX knockdown on surface markers expression, viability and phagocytosis of macrophages. (A) Left panel: Flow cytometry analysis of indicated surface markers in monocytes transfected with siGFP or siVentX, respectively; right panel: bar graphs show the mean+SD of at least three separate experiments. *$p<0.05$; **$p<0.01$. (B) Effects of VentX knockdown on macrophage viability. Monocytes were transfected with either siGFP or siVentX and subsequently exposed to 100 ng/mL M-CSF for 3 days. Cells were then harvested and stained with PI and Annexin V and analyzed by flow cytometry. (C) Effects of VentX knockdown on phagocytosis. Monocytes were transfected with siGFP or siVentX. Phagocytosis assays were carried out as described in materials and methods. Red histogram represents transfection with siGFP; green histogram represent transfection with siVentX. Left panel: cells were incubated on ice; right panel: cells were incubated at 37° C. Representative data of three independent experiments are shown.
Figure 3:
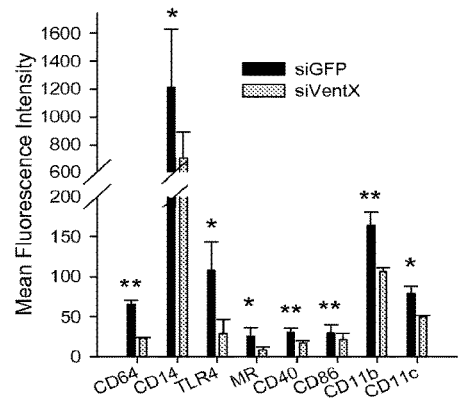
Figure 3:
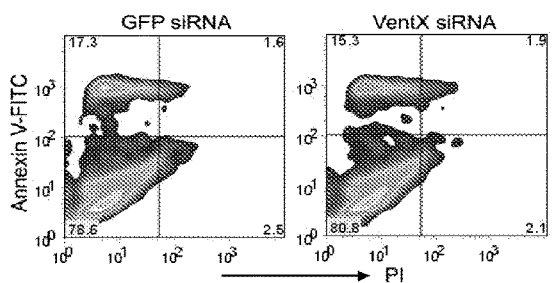
Figure 3:
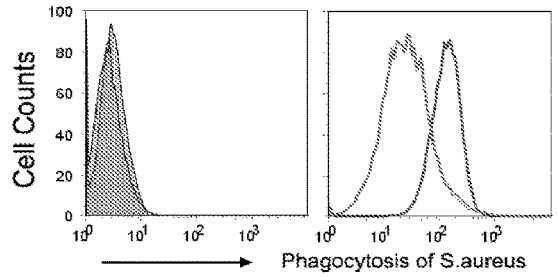
Figure 12:
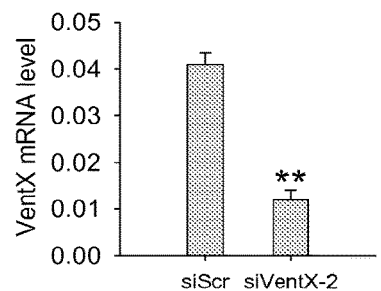
FIG. 12 shows exemplary knockdown of VentX with a different siRNA sequence reduces terminal monocyte to macrophage differentiation. Monocytes were transfected with either a scrambled sequence of siRNA (Scr siRNA) or VentX siRNA-2 (5'-UCUACUCAACGUCUUCUGGC-CUUGCCAAU-3')(SEQ ID NO:3) through electroporation. Mock transfection that did not include siRNA was also conducted as control. Overnight after transfection, cells were exposed to 100 ng/mL M-CSF to trigger their macrophagic differentiation. (A) At 3 days after transfection, cells were collected to analyze the efficiency of VentX knockdown by real-time PCR. (B) At 4 days after transfection, FACS analysis was performed with cells stained with PE-conjugated anti-CD71antibody. (C) Cells were stained with PE-conjugated anti-CD14, CD64, TLR4, CD80 and CD11c.
Figure 12:
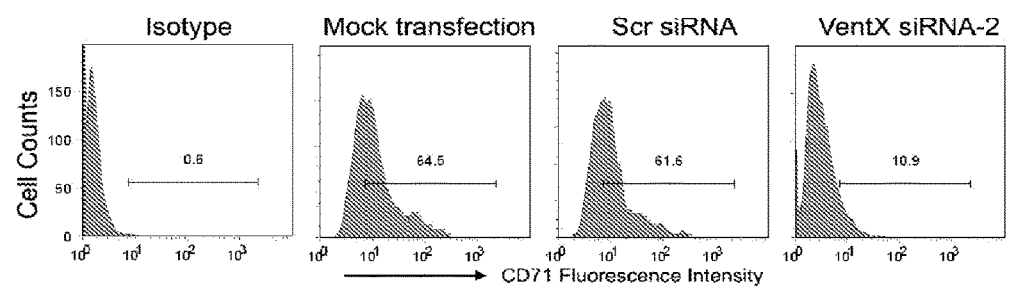
Figure 12:
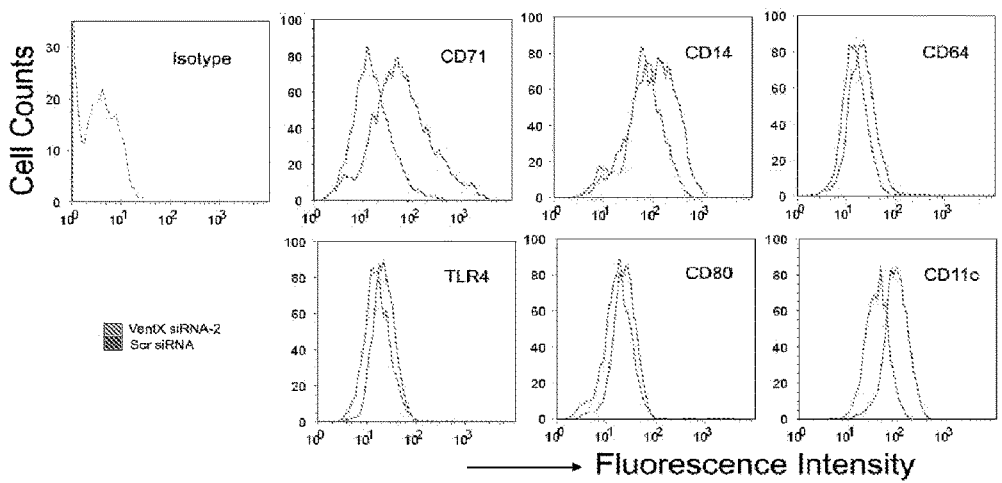
Figure 13:
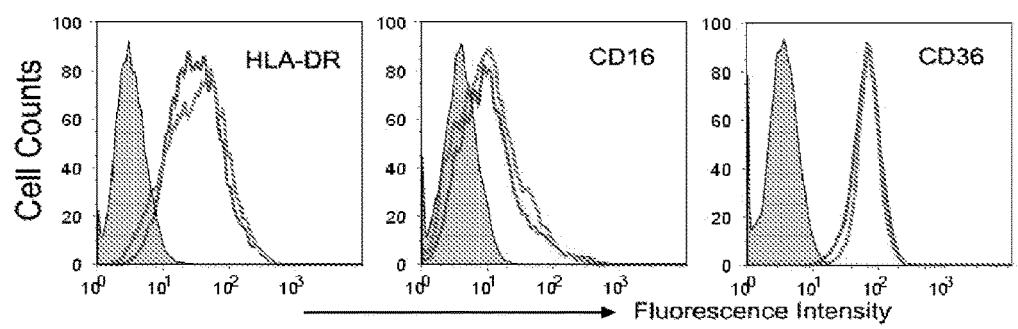
FIG. 13 shows exemplary FACS analysis of monocyte phenotypes after VentX knockdown. Monocytes were transfected with either siGFP or siVentX and subsequently exposed to 100 ng/mL M-CSF to trigger their macrophagic differentiation. At 4 days after transfection, cells were collected and stained with indicated antibodies followed by FACS analysis.
Figure 14:
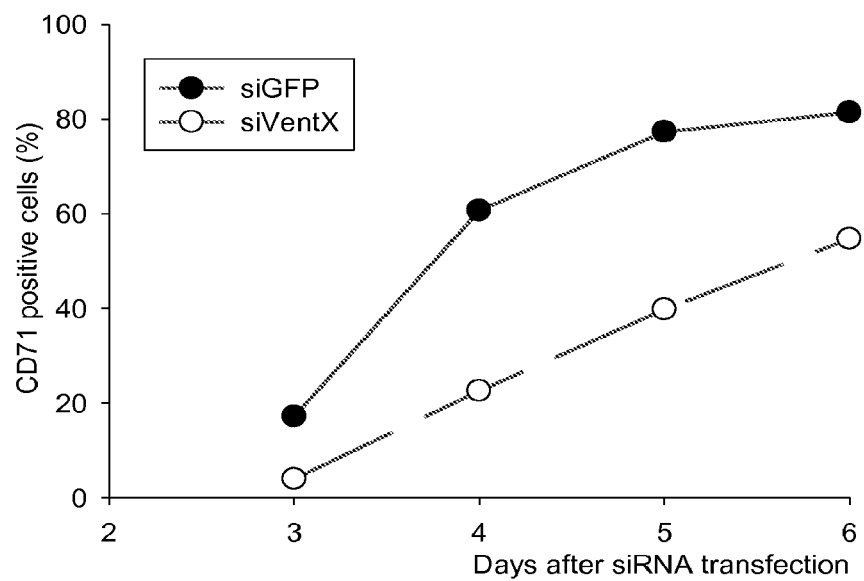
FIG. 14 shows exemplary time-course expression of CD71 in primary monocytes after VentX knockdown. Monocytes were transfected with either siGFP or siVentX and subsequently exposed to 100 ng/mL M-CSF to trigger their macrophagic differentiation. Surface expression of CD71 was determined by FACS analysis at indicated days after siRNA transfection. Upper panel shows the percentage of CD71 positive cells and lower panel shows the normalized MFI of CD71 staining.
Figure 14:
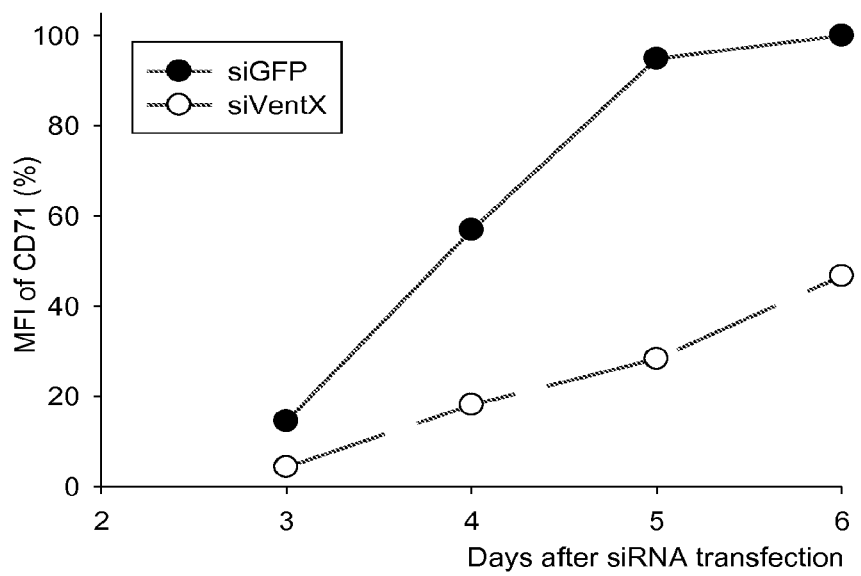

The increased expression of VentX during monocyte to macrophage differentiation suggests a potential role for VentX during the process. To address this hypothesis, small interfering RNA (siRNA) technology was employed to knock down VentX expression in primary monocytes. The efficacy of siVentX was determined by quantitative PCR and western blot analysis (FIG. 2A). In vitro differentiation of peripheral blood monocytes to macrophages by M-CSF stimulation is accompanied by elongated or fibroblast-like morphology and the expression of cell surface CD71 antigen, a macrophagic differentiation marker. (van Grevenynghe, et al. 2003 *J Immunol* 170:2374-2381; Andreesen, et al. 1984 *Blut* 49:195-202; Scheuerer, et al. 2000 *Blood* 95:1158-1166; Rebe, et al. 2007 *Blood* 109:1442-1450; Gessani, et al. 1993 *J Immunol* 151:3758-3766; Cathelin, et al. 2006 *J Biol Chem* 281:17779-17788; Young, et al. 1990 *J Immunol* 145:607-615.) As shown in FIG. 2B, knockdown of VentX expression in monocytes abrogated the morphogenesis of the fibroblast-like shape (FIG. 2B) and substantially diminished the expression of cell surface CD71 marker triggered by M-CSF treatment (FIG. 2C-D). Other macrophage phenotypic markers such as FcγRI CD64, co-stimulatory molecules CD40 and CD86, and integrins CD11b and CD11c were also significantly down-regulated in siVentX transfected monocytes compared with siGFP transfected control cells (FIG. 3A). In support of its functional relevance in innate immunity, the expression of pattern recognition receptors such as TLR4 (Toll-like receptor 4), MR (mannose receptor), and CD14 was also down-regulated in VentX silenced cells (FIG. 3A). To eliminate the possibility of off-target effects, a second siRNA sequence (VentX siRNA-2) was used that has been shown to be effective in knockdown of VentX expression. (Gao, et al. 2010 *Cancer Res* 70:202-211.) As shown in FIG. 12, surface expression of CD71 and other markers was again down-regulated by VentX siRNA-2 but not by a scrambled siRNA. It should be noted, however, not all macrophage surface molecules are affected by the knockdown of VentX. For example, expression of HLA-DR, CD16 and CD36 remained unchanged after VentX knockdown (FIG. 13). Moreover, VentX knockdown did not decrease the viability of primary monocytes as determined by propidium iodide (PI) and Annexin V staining assay (FIG. 3B), therefore, ruling out the possibility that diminished monocyte to macrophage differentiation may result from cytotoxicity induced by VentX suppression. The effect of VentX knockdown on macrophage differentiation could be seen as early as 3 days after siRNA transfection and was still noticeable 6 days after transfection (FIG. 14). In addition to M-CSF, siVentX blocked macrophage differentiation by other known inducing factors, such as GM-CSF or IL3 (25, 31) (FIG. 15). (van Grevenynghe, et al. 2003 *J Immunol* 170:2374-2381; Young, et al. 1990 *J Immunol* 145:607-615.) Monocyte to macrophage differentiation is associated with enhanced capability of phagocytosis. (Serbina, et al. 2008 *Annu Rev Immunol* 26:421-452.) As shown in FIG. 3C, in comparison with the control, monocytes transfected with siVentX displayed reduced phagocytic activity, suggesting that VentX is required for functional development during monocyte to macrophage differentiation.

VentX Promotes Macrophage Differentiation of U937 Cells

Figure 4:
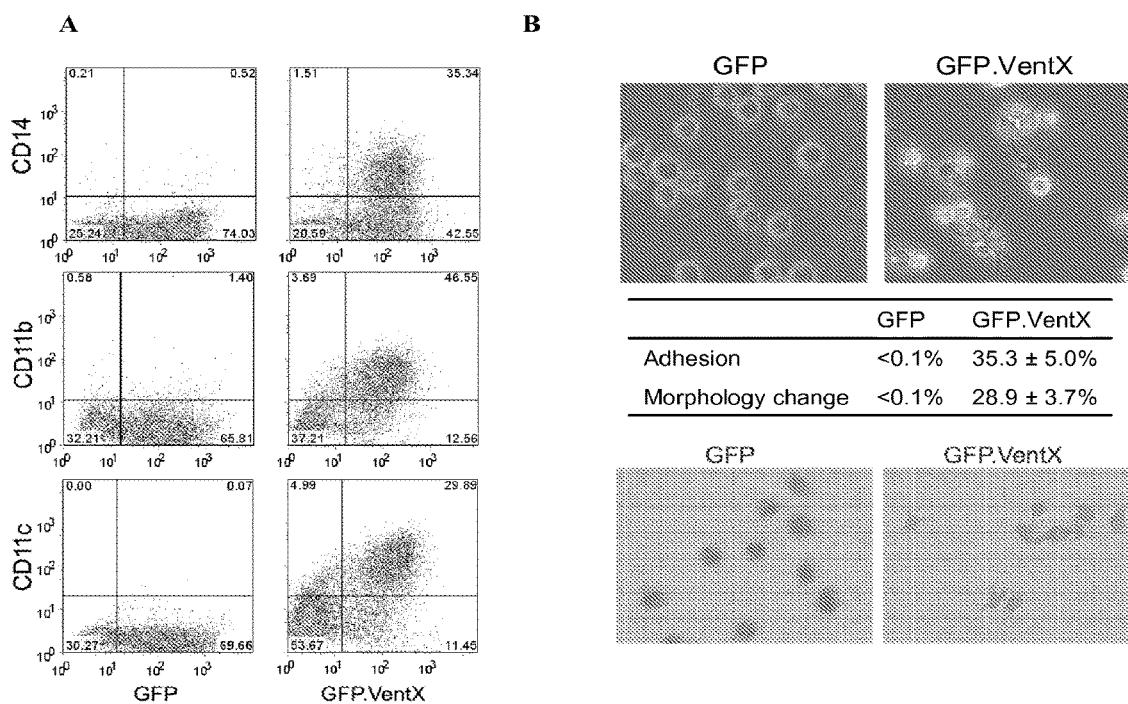
FIG. 4 shows that VentX promotes macrophage differentiation of U937 cells. U937 cell lines conditionally expressing GFP or GFP.VentX under the control of a tetracycline-inducible promoter were treated with 1.0 µg/mL doxycycline (DOX) for 72 hours. (A) FACS analysis of monocyte/macrophage surface markers of CD 14, CD11b, and CD11c. (B) Effects of VentX expression on morphogenesis and adhesion of U937 cells. Upper panel: cells were photographed using phase contrast microscopy. The percentage of cells on adhesion was calculated by methods of trypsinization and counting both floating and adherent fractions of cells. Cells showing pseudopodia were counted as cells with morphological change. Lower panel: Wright-Giemsa staining of DOX-treated U937 cells. Magnification: ×200.
Figure 16:
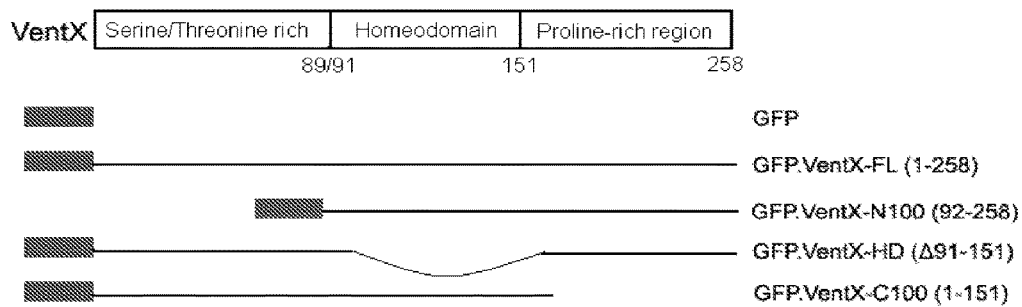
FIG. 16 shows that Homeodomain (HD) of VentX is essential for inducing macrophagic differentiation in U937 cells. (A) A schematic diagram depicts various truncated VentX constructs (all in pRetroX-Tight-Puro retroviral vector) used in this study. (B) The U937 cell lines conditionally expressing three truncated VentX were generated as described in Materials and Methods. Cell surface markers were detected by FACS analysis after 3 days exposure to 1.0 μg/mL DOX.
Figure 16:
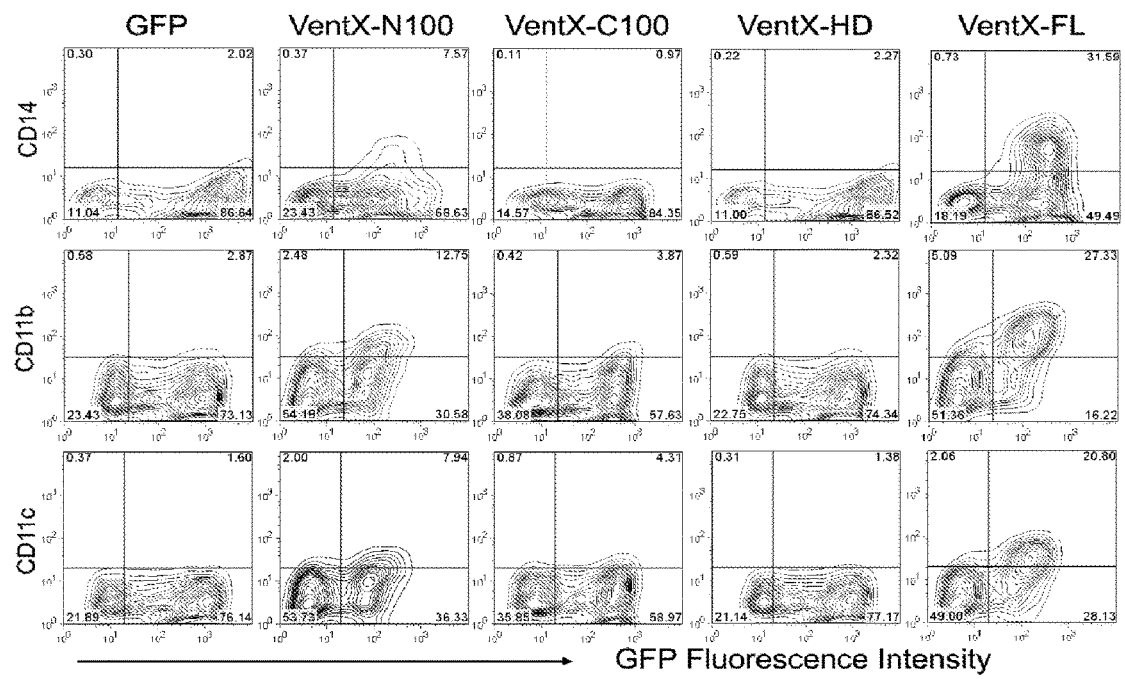

U937 is a promonocytic cell line that has been widely used as a model to study monocyte to macrophage differentiation. It has been shown that ectopic expression of several transcription factors, such as BLIMP-1 and IRF-7, was able to trigger macrophage differentiation in U937. (Lu, et al. 2001 *J Biol Chem* 276:45491-45496; Chang, et al. 2000 *Nat Immunol* 1:169-176.) To test whether VentX is a bona fide key regulator of monocyte to macrophage differentiation, stable U937 cell lines was generated expressing GFP or GFP.VentX under the control of doxycycline (DOX)-inducible promoter. As shown in FIG. 4A, after 3 days of DOX induction, a large portion of U937 cells became GFP positive. In the GFP.VentX transduced cells, more than 50% of GFP positive cells acquired surface expression of CD11b, CD11c, and CD14, the markers of macrophage differentiation (18, 25, 32); whereas few GFP transduced cells obtained these markers (FIG. 4A). (Chang, et al. 2000 *Nat Immunol* 1:169-176; van Grevenynghe, et al. 2003 *J Immunol* 170:2374-2381; Ragg, et al. 1998 *J Immunol* 161:1390-1398.) Truncation analysis showed that the pro-differentiation function of VentX depends on its DNA-binding homeodomain (FIG. 16). In addition to the acquisition of surface markers, ectopic expression of VentX also led to pronounced morphology changes in U937 cells. As shown in FIG. 4B, after 3 days of induction, GFP.VentX transduced cells became adherent and flattened with extensive pseudopodia, resembling the morphology after ectopic expression of BLIMP-1. (Chang, et al. 2000 *Nat Immunol* 1:169-176.) In contrast, no such phenotypes were observed in U937 cells expressing GFP. Further, enhanced phagocytotic activity (FIG. 5A) and increased expression (FIG. 5B) and secretion (FIG. 5C) of pro-inflammatory cytokines were also detected in GFP.VentX transduced U937 cells, suggesting a role of VentX in the pro-inflammatory response of macrophages. Terminal macrophage differentiation of U937 cells is usually coupled with the cessation of cell division. Indeed, it was observed that GFP.VentX transduced U937 cells were associated with apparent G1 growth arrest (FIG. 5D-E), which is likely ascribed to the downregulation of c-Myc and upregulation of p21 after VentX expression (FIG. 5F).

VentX Controls the Expression of M-CSF Receptor

Figure 7:
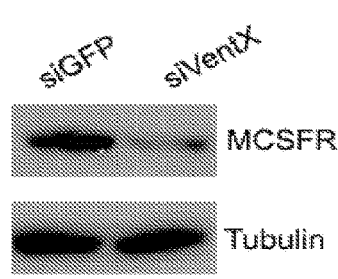
FIG. 7 shows that VentX regulates M-CSFR expression in primary monocytes. (A-C) Freshly isolated monocytes were transfected with siRNA against GFP or VentX respectively. Cells were then maintained in RPMI 1640 medium supplied with M-CSF and harvested at 3 days post-transfection. (A) Protein level of M-CSFR in transfected cells was determined by western blotting analysis. (B) Surface expression of M-CSFR was determined by FACS analysis. Filled gray histogram represents isotype control; solid line histogram represents transfection with siGFP; dotted line histogram represents transfection with siVentX. (C) M-CSFR mRNA level in transfected cells was determined by real-time PCR. Data represent mean+SD of triplicates of one representative experiment. (D) ChIP analysis of VentX effects on the interaction between Foxp1 and M-CSFR promoter in U937 cells (upper panel) and primary monocytes (lower panel) by overexpression (upper panel) and knockdown (lower panel) approaches. Note, VentX did not affect the interaction between Foxp1 and M-CSFR promoter region.
Figure 7:
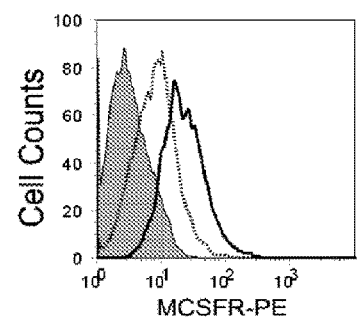
Figure 7:
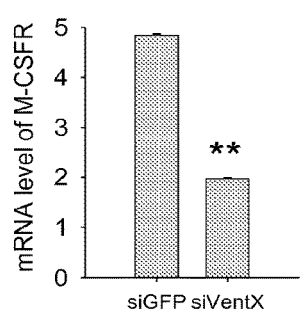
Figure 7:
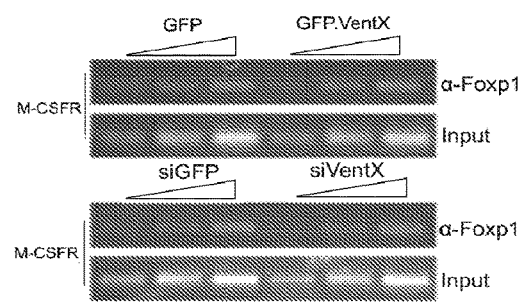
Figure 17:
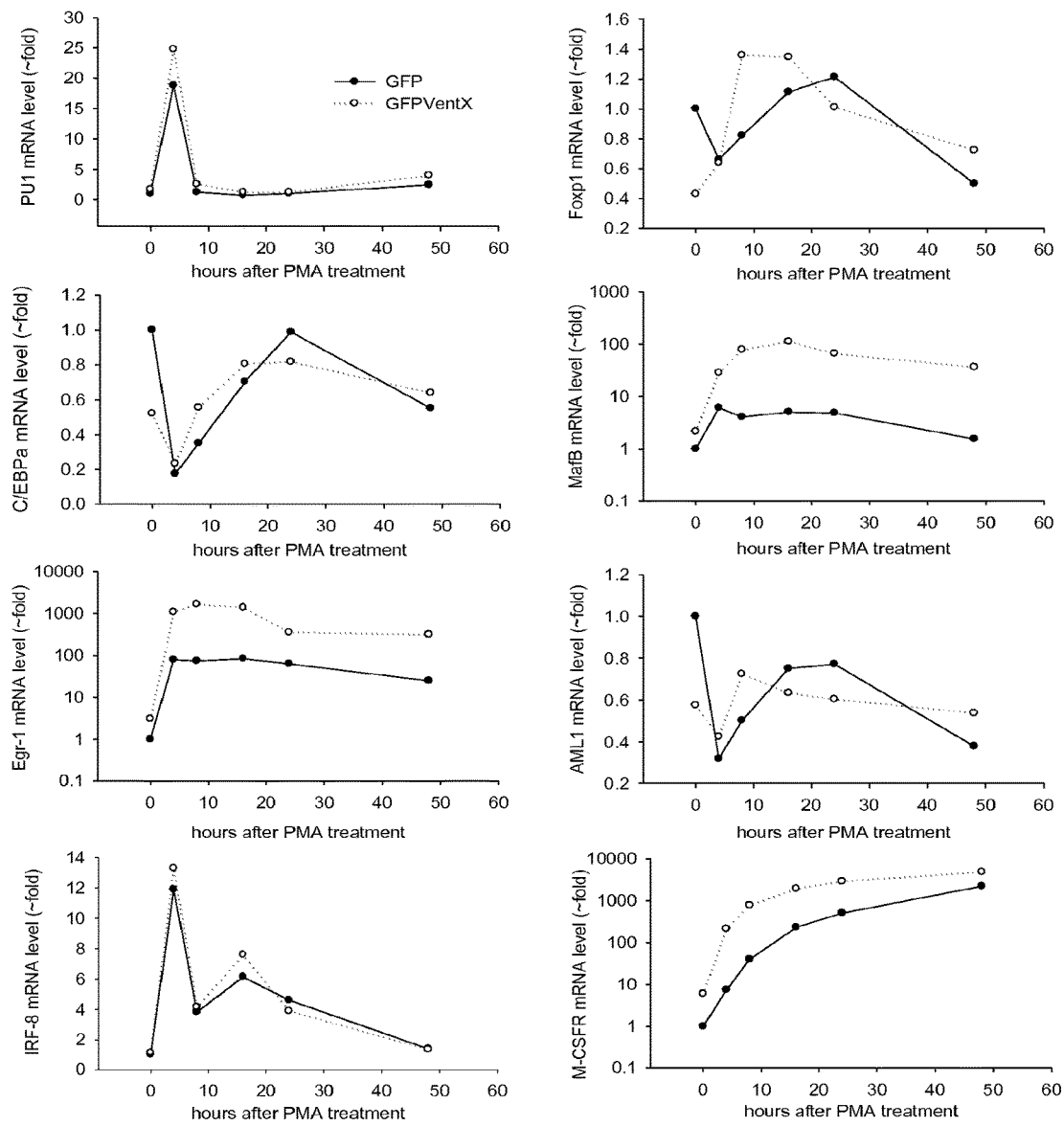
FIG. 17 shows exemplary screening for downstream targets of VentX associated with monocyte differentiation in HL60 cells. HL60 cells were transfected with plasmids encoding GFP or GFPVentX. Positively transfected cells were sorted and treated with 10 nM PMA to induce monocytic differentiation. At indicated time points after PMA treatment, cells were harvested for quantitative analysis of mRNA level of PU1, Foxp1, C/EBPα, MafB, Egr-1, AML1, IRF-8 and M-CSFR. The value at zero time point was designated as 1.0.
Figure 19:
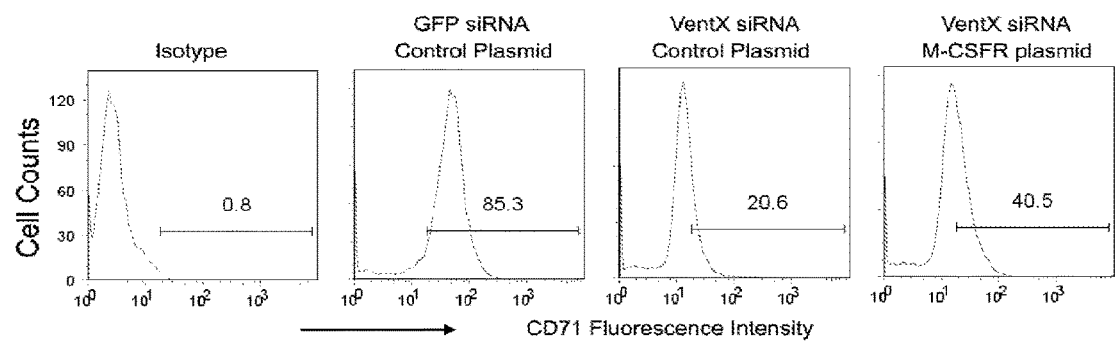
FIG. 19 shows exemplary complementation of M-CSF receptor partially rescued macrophage differentiation defect in VentX siRNA transfected monocytes. Freshly isolated monocytes were transfected with the indicated combination of siRNA and plasmid through electroporation. At 4 days after transfection, cells were harvested and stained with anti-CD71 antibody followed by FACS analysis.

Multiple signaling pathways and transcription factors have been implicated in monocyte differentiation. (Friedman 2007 *Oncogene* 26:6816-6828.) To identify potential targets of VentX during monocyte differentiation, HL60 cells were ectopically expressed with VentX and treated with phorbol myristate acetate (PMA) to induce monocytic differentiation. (Rovera, et al. 1979 *Proc Natl Acad Sci USA* 76:2779-2783.) As shown in FIG. 17, VentX induced drastic upregulation of M-CSF receptor (M-CSFR) and transcription factors MafB and Egr-1 in HL60 cells. No apparent changes were observed for CCAAT enhancer-binding protein (C/EBP), AML1, IRF8, Foxp1 and PU.1, the master regulator of myeloid development (FIG. 17). Previous studies showed that M-CSFR is absolutely required for macrophage differentiation and is a downstream target of multiple myeloid transcriptional factors. (Dai, et al. 2002 *Blood* 99:111-120.) Focused was placed on the potential regulation of M-CSFR by VentX, using gain- and loss-of-function approaches. Over-expression of VentX in U937 cells resulted in induction of M-CSFR as determined by western blotting analysis of total cellular lysates (FIG. 6A) and surface expression by flow cytometry analysis (FIG. 6B). M-CSFR mRNA was also dramatically elevated as determined by real time PCR (FIG. 6C). To elaborate the mechanisms underlying VentX induced M-CSFR expression, the effects of VentX on M-CSFR transcription were examined. Using M-CSFR promoter luciferase reporter assays, it was observed that VentX significantly augmented M-CSFR promoter activity in U937 cells (FIG. 6D MCSFR/WT). In comparison, VentX did not affect the activity of a control pGL3 luciferase reporter in this cell line. Detailed examination of the human M-CSFR promoter region revealed a putative homeodomain binding site (HDB) (FIG. 7A). (Laughon 1991 *Biochemistry* 30:11357-11367.) Mutations of the HDB site in the M-CSFR promoter resulted in a significant decrease in VentX-induced luciferase activity, suggesting the functional importance of the HDB site (FIG. 6D, MCSFR/Mut). To determine whether VentX interacts with the M-CSFR promoter directly, chromosome immunoprecipitation (ChIP) assay and electrophoretic mobility shift assay (EMSA) were performed. The results of both tests suggested a direct interaction between VentX and M-CSFR promoter (FIG. 6E-F). Moreover, the interaction between VentX and M-CSFR promoter was largely abrogated by mutation of the HDB sites as revealed by the EMSA assay (FIG. 6F lane 3), suggesting the importance of the HDB in mediating interaction between VentX and M-CSFR promoter. It was then examined whether VentX is also required for M-CSFR expression in primary monocytes. To this end, endogenous VentX was knocked down in primary monocytes by siRNA method. In support of the over-expression experiments in U937 cell model, knockdown of VentX in primary monocytes caused significant downregulation of M-CSFR at mRNA, protein as well as cell surface expression levels (FIG. 7A-C). To further assess the potential role of M-CSFR in mediating VentX function, M-CSFR plasmid was co-transfected with VentX siRNA into primary monocytes. As shown in FIG. 19, ectopic expression of M-CSFR partially restored the macrophage differentiation defect caused by VentX knockdown, suggesting that VentX regulates monocyte to macrophage differentiation, at least in part, through modulating the expression of M-CSF receptor.

Figure 18:
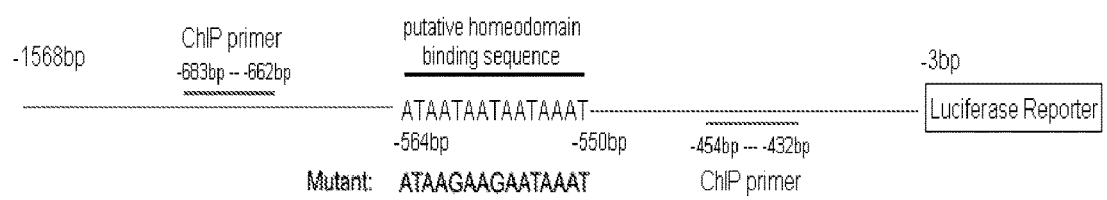
FIG. 18 shows (A) Schematic diagram depicts promoter region of M-CSF receptor (SEQ ID NO:10). A mutant binding sequence is shown as SEQ ID NO:11. (B) Schematic diagram showing different transcriptional factors binding sites on M-CSFR promoter region.
Figure 18:
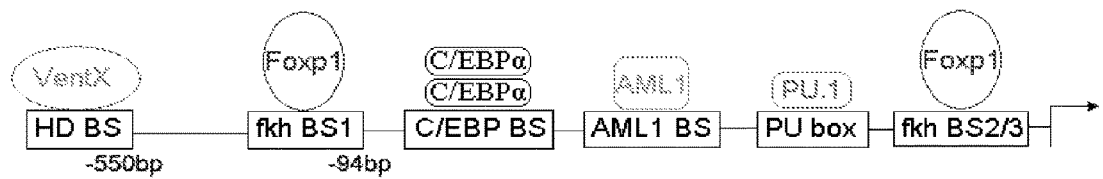

Previous studies showed that the M-CSFR promoter is subjected to the regulation of multiple other transcriptional factors such as Foxp1, PU.1, AML1 and C/EBP. (Bonifer, et al. 2008 *Front Biosci* 13:549-560.) In particular, Foxp1 binds to the forkhead binding sites within M-CSFR promoter and operates as a transcriptional repressor of M-CSFR expression, which raised a possibility that VentX may promote M-CSFR expression through displacement of Foxp1 occupancy on the M-CSFR promoter. (Shi, et al. 2004 *J Clin Invest* 114:408-418.) To test this hypothesis, ChIP assays were performed to detect the interaction between Foxp1 and the M-CSFR promoter in U937 cells with ectopic expression of VentX and in primary monocytes with knockdown of VentX. As shown in FIG. 7D, neither over-expression nor knockdown of VentX affected the binding of Foxp1 to the M-CSFR promoter, as shown by the ChIP assays. Notably, the binding site of VentX on the M-CSFR promoter is distant (~450 bp) to that of Foxp1 (FIG. 18B).

VentX is Required for the Pro-Inflammatory Response in Macrophages

Figure 9:
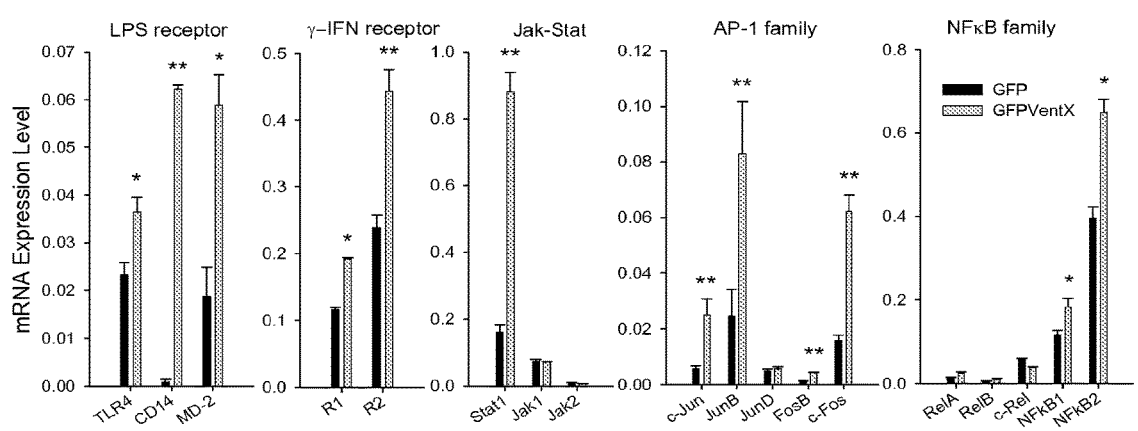
FIG. 9 shows exemplary results of VentX regulating LPS and IFN-γ signaling pathways. (A) Effects VentX overexpression on the expression of LPS and IFN-γ pathways components. U937 cells expressing GFP or GFP.VentX under the control of a tetracycline inducible promoter were treated with 1 µg/mL LPS for 6 hours after exposure to DOX for 72 hours. Real-time PCR was performed to determine mRNA levels of the indicated genes. Data represent mean+SD of two separate experiments. (B) Effects of VentX knockdown on the expression of LPS and IFN-γ pathways components. Macrophages were transfected with siGFP or siVentX, respectively, followed by culture in RPMI 1640 medium for 3 days. Cells were then exposed to 1 µg/mL LPS plus 20 ng/mL γ-IFN for 6 hours. Real-time PCR was performed to determine mRNA levels of the indicated genes. Data represent mean+SD of triplicates of one representative experiment. (C) FACS analysis of surface expression of CD119, CD14 and TLR4 from macrophages transfected with siGFP or siVentX. Filled blue histogram represent the isotype control staining; red histogram represent macrophages transfected with siGFP; green histogram represent macrophages transfected with siVentX. (D) Western blot analysis of VentX effects on the protein level of STAT1, JunB and c-Fos genes in U937 cells (left column) and macrophages (right column) by overexpression and knockdown approaches, respectively. (E) ChIP analysis of VentX interaction with STAT1 and JunB promoter regions. No significant binding of VentX to the promoter regions of STAT1 and JunB was detected by the ChIP assay.
Figure 9:
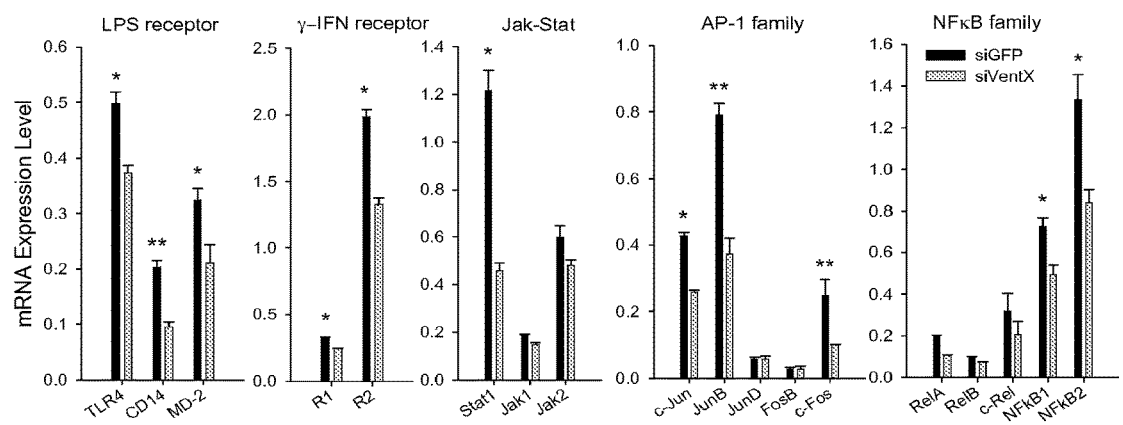
Figure 9:
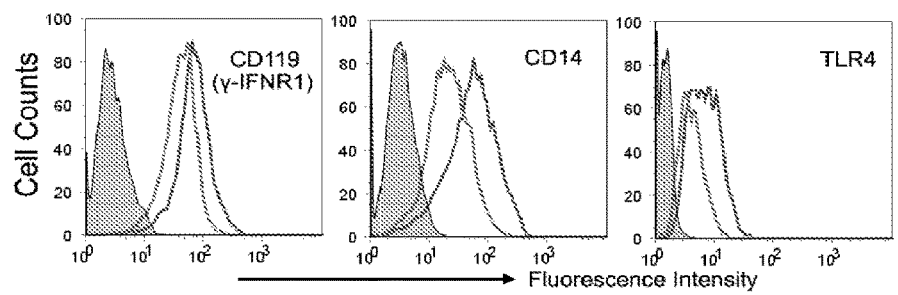
Figure 9:
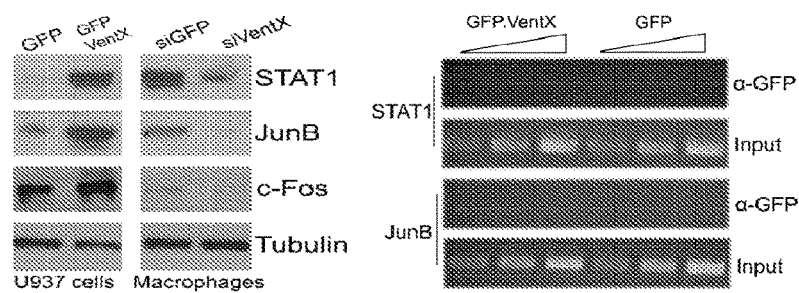
Figure 20:
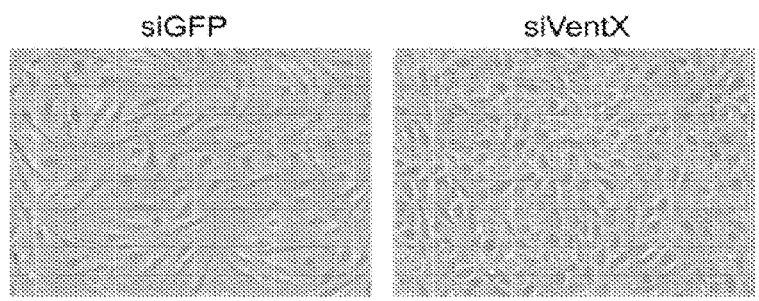
FIG. 20 shows exemplary analysis of macrophage phenotypes after VentX knockdown. Macrophages were derived from fresh monocytes by incubation with 100 ng/mL M-CSF for 4 days. Macrophages were then collected and transfected with siGFP or siVentX, respectively, and further incubated in M-CSF culture for 3 days. (A) The photographs of cells were taken directly in culture using phase-contrast microscopy. The percentage of cells with adhesion was calculated as described in FIG. 3B. The percentages of cells with a fibroblastic shape were counted as cells with morphological change. (B) Macrophages were harvested and stained with indicated antibodies followed by FACS analysis.
Figure 20:
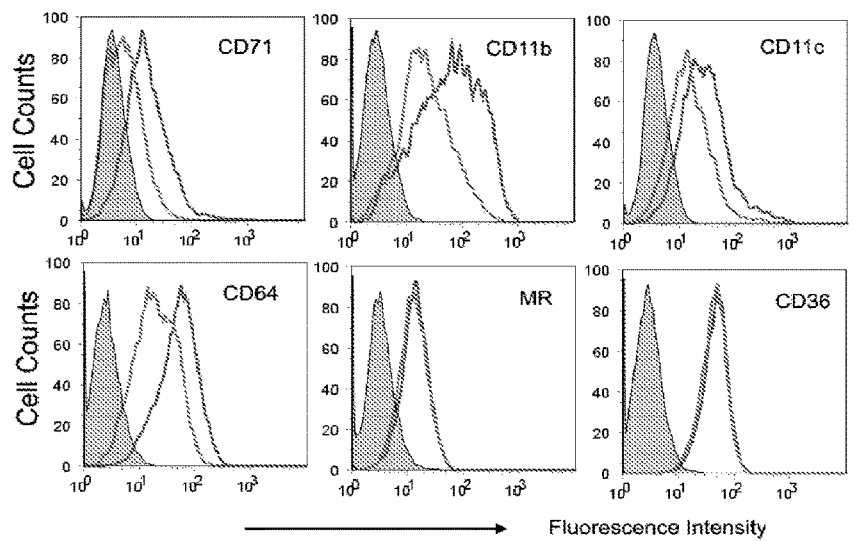

Macrophages retain a high level of VentX expression (FIGS. 1B and D). The requirement of VentX for macrophage functions was explored. It was found that, upon knockdown of VentX expression, macrophages lost their adherence to a plastic surface and were not able to spread out and maintain their fibroblast-like shapes (FIG. 9A). The morphological changes of macrophages were associated with significant decreases in levels of cell surface adhesion molecules such as CD11b and CD11c, as determined by flow cytometry analysis (FIG. 20B), which may account for their aberrant morphologies. (Imhof, et al. 2004 *Nat Rev Immunol* 4:432-444.)

Macrophages classically activated in vitro by IFN-γ and LPS stimulation display elevated expression of MHC-II and co-stimulatory molecules CD80 and CD86, secrete high level of pro-inflammatory cytokines, and exhibit enhanced antimicrobial activity. (Martinez, et al. 2008 *Front Biosci* 13:453-461; Mosser, et al. 2008 *Nat Rev Immunol* 8:958-969.) To investigate whether VentX is required for classical activation of macrophages, a loss-of-function approach by knockdown of VentX was used. First, it was found that surface expression of CD40, CD80 and CD86, but not the HLA-DR, was significantly down-regulated in macrophages transfected with siVentX (FIG. 8A). Second, expression of pro-inflammatory cytokines such as TNFα, IL1β, IL6, IL8 and IL12, as well as M-CSF were significantly decreased in cells transfected with siVentX (Table 1). Consistently, there was a significant reduction in pro-inflammatory cytokine secretion by these siVentX transfected macrophages (FIG. 8B). Third, siVentX-transfected macrophages produced significantly less reactive oxygen species (FIG. 8C) and nitric oxide (FIG. 8D), and displayed a much weaker phagocytotic capability (FIG. 8E), suggesting these cells are less effective in microbial killing. In addition, siVentX transfected macrophages were less potent to stimulate allogeneic T cells proliferation, reflecting a decreased antigen presentation capability (FIG. 8F). Taken together, these experiments suggest that VentX is required for the macrophage classical activation.

TABLE 1

Effects of VentX knockdown on cytokine mRNA expression in macrophages

|  | siGFP | siVentX | p Value |
|---|---|---|---|
| TNF-α | 0.46 ± 0.04 | 0.18 ± 0.01 | <0.01 |
| IL6 | 3.40 ± 0.21 | 1.78 ± 0.14 | <0.01 |
| M-SCSF | 0.40 ± 0.01 | 0.14 ± 0.01 | <0.01 |
| IL12p35 | 1.77 ± 0.21 | 0.37 ± 0.14 | <0.01 |
| IL12p40 | 0.52 ± 0.02 | 0.61 ± 0.05 | >0.05 |
| IL8 | 471 ± 10.2 | 172 ± 5.8 | <0.01 |
| IL1-β | 51.08 ± 3.2 | 21.93 ± 1.8 | <0.01 |

Figure 21:
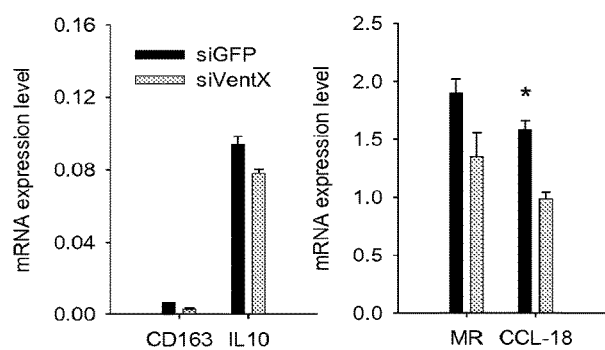
FIG. 21 shows that VentX is not essential for macrophage alternative activation. Macrophages were treated as described in FIG. 22. 100 ng/ml of IL4 was added to culture 24 h before harvest. (A) Total RNA was isolated to analyze the mRNA level of CD163, IL10, MR and CCL-18 by real-time PCR. (B) Cells were harvested and stained by anti-MR and anti-CD163 antibodies followed by FACS analysis.
Figure 21:
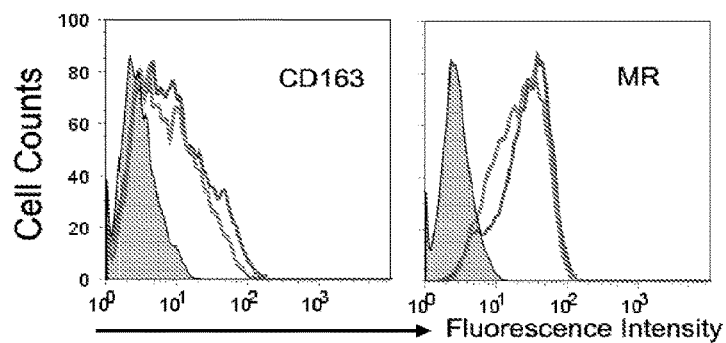

Also investigated was whether VentX regulates the macrophage alternative activation following IL4 treatment by analyzing several alternative activation markers such as CD163, MR (mannose receptor), AMAC1 (alternative macrophage activation-associated CC chemokine 1; also called CCL-18) and IL10. (Gordon 2003 *Nat Rev Immunol* 3:23-35; Bouhlel, et al. 2007 *Cell Metab* 6:137-143.) As shown in FIG. 21, although the level of CCL-18 was downregulated, the expression of CD163, MR and IL10 was not significantly affected by VentX knockdown. Hence, VentX appears not to be essential for alternative activation of macrophages by IL4.

VentX Targets Multiple Pathways to Regulate the Pro-Inflammatory Response in Macrophage LPS and IFN-γ are two key stimuli to trigger the pro-inflammatory response of macrophages (2, 3). (Martinez, et al. 2008 *Front Biosci* 13:453-461; Mosser, et al. 2008 *Nat Rev Immunol* 8:958-969.) Therefore, also investigated was whether VentX affected the signaling pathways of these two stimulants. First examined was whether VentX affected the expression of membrane receptors for LPS and IFN-γ. Using the U937 cell model, it was found that ectopic expression of VentX significantly increased mRNA level of the LPS receptor components (TLR4, CD14, MD-2) and IFN-γ receptors (R1 and R2) (FIG. 9A). Knockdown of VentX in primary macrophages consistently reduced the mRNA level of these receptors (FIG. 9B). Flow cytometry analysis further confirmed that surface expression of CD119 (IFN-γ receptor 1), CD14 and TLR4 was significantly diminished in siVentX transfected macrophages (FIG. 9C).

The TLR4 pathway is coupled to the activation of cytoplasmic transcription factors such as NF-κB and AP-1, which translocate to the nucleus and trigger profound changes in macrophage gene expression. (Schroder, et al. 2006 *Immunobiology* 211:511-524; Aderem, et al. 2000 *Nature* 406:782-787.) The IFN-γ signaling is largely mediated by the latent cytosolic factor Stat1 (signal transducer and activator of transcription-1) that is activated during IFN-γ dependent Jak-Stat pathway. (Schroder, et al. 2006 *Immunobiology* 211:511-524; Hu, et al. 2007 *J Leukoc Biol* 82:237-243; Schroder, et al. 2004 *J Leukoc Biol* 75:163-189.) Thus, whether VentX targeted components of TLR4 and IFN-γ downstream signaling pathways was examined. As shown in FIGS. 9A and B, both gain of function experiments in U937 cells (FIG. 9A) and loss-of-function experiments in primary macrophages (FIG. 9B) demonstrated that VentX regulated the expression of multiple members of Jak-Stat, AP-1 and NF-κB signaling pathways. Particularly, mRNA levels of Stat1, Jun-B and c-Fos were substantially affected by the altered VentX expression (FIG. 9A-B). The mRNA data were further confirmed by western blotting analysis, which showed that the protein levels of Stat1, Jun-B and c-Fos were subjected to modulation by VentX (FIG. 9D). To explore the mechanisms whereby VentX regulates these factors, ChIP assays were performed but revealed no significant binding of VentX to the promoter regions of these genes (FIG. 9E), suggesting that VentX may regulate their expression indirectly.

Figure 10:
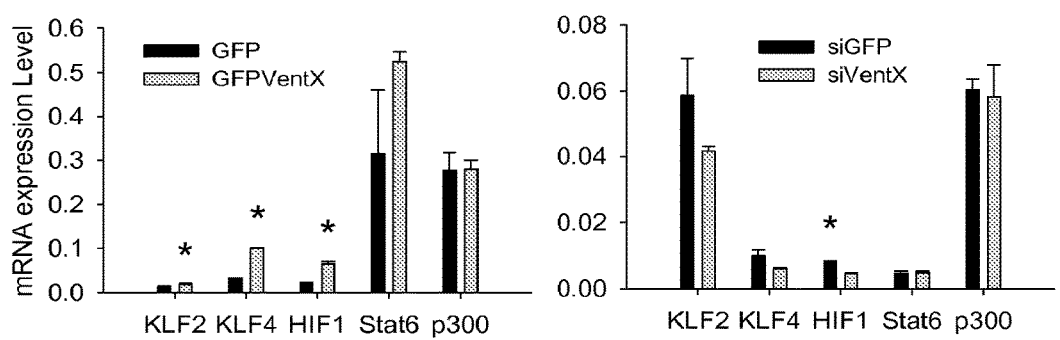
FIG. 10 shows exemplary effects of VentX on the mRNA level of additional genes implicated in macrophage activation. VentX expressions in U937 cells and macrophages were modulated as described in FIG. 9. The mRNA levels of indicated genes were determined by real-time PCR.
Figure 22:
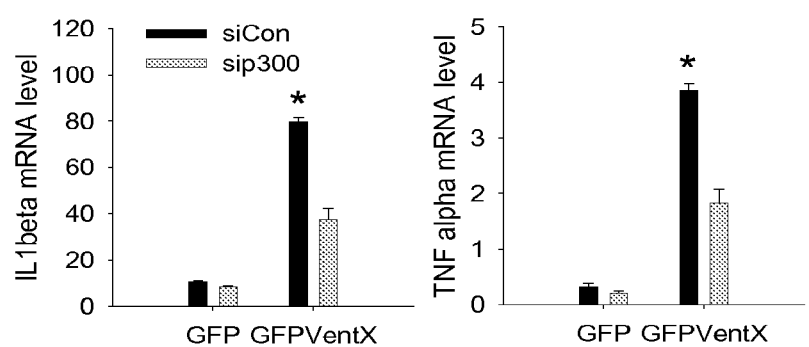
FIG. 22 shows that p300 is required for VentX induced pro-inflammatory response in U937 cells. U937 cells were first transfected with p300 siRNA or control siRNA through electroporation. At 24 hours after transfection, cells were treated with DOX to induce GPF or GFPVentX expression. At 72 hours after transfection, cells were harvested to determine mRNA level of TNF-α and IL1-β.

Multiple other transcriptional factors are also implicated in macrophage activation by previous studies. For example, Kruppel-like factor (KLF4) and hypoxia-inducible factor (HIF-1) are suggested to promote macrophage activation, whereas KLF2 and Stat6 are inhibitory. (Feinberg, et al. 2005 *J Biol Chem* 280:38247-38258; Das, et al. 2006 *Proc Natl Acad Sci USA* 103:6653-6658; Cao, et al. 2010 *Blood* 116:4404-4414; Kawanami, et al. 2009 *J Biol Chem* 284:20522-20530; Lentsch, et al. 2001 *J Clin Invest* 108:1475-1482; Murdoch, et al. 2005 *J Immunol* 175:6257-6263.) In addition, emerging evidence has suggested the involvement of the transcriptional co-activator p300/CBP in the activation of macrophages. Whether VentX regulates the expression of these factors was examined. As shown in FIG. 10, while over-expression of VentX augmented mRNA levels of KLF2, KLF4 and HIF-1 in U937 cells, knockdown of VentX only caused downregulation of HIF-1 mRNA in primary macrophages, suggesting HIF-1 may be a physiological downstream target of VentX. VentX did not regulate the expression of p300 mRNA (FIG. 10). However, when p300 was knocked down in U937 cells, VentX-induced upregulation of TNF-α and IL1-β became significantly compromised (FIG. 22), suggesting that p300 is involved in the VentX induced pro-inflammatory response.

Figure 11:
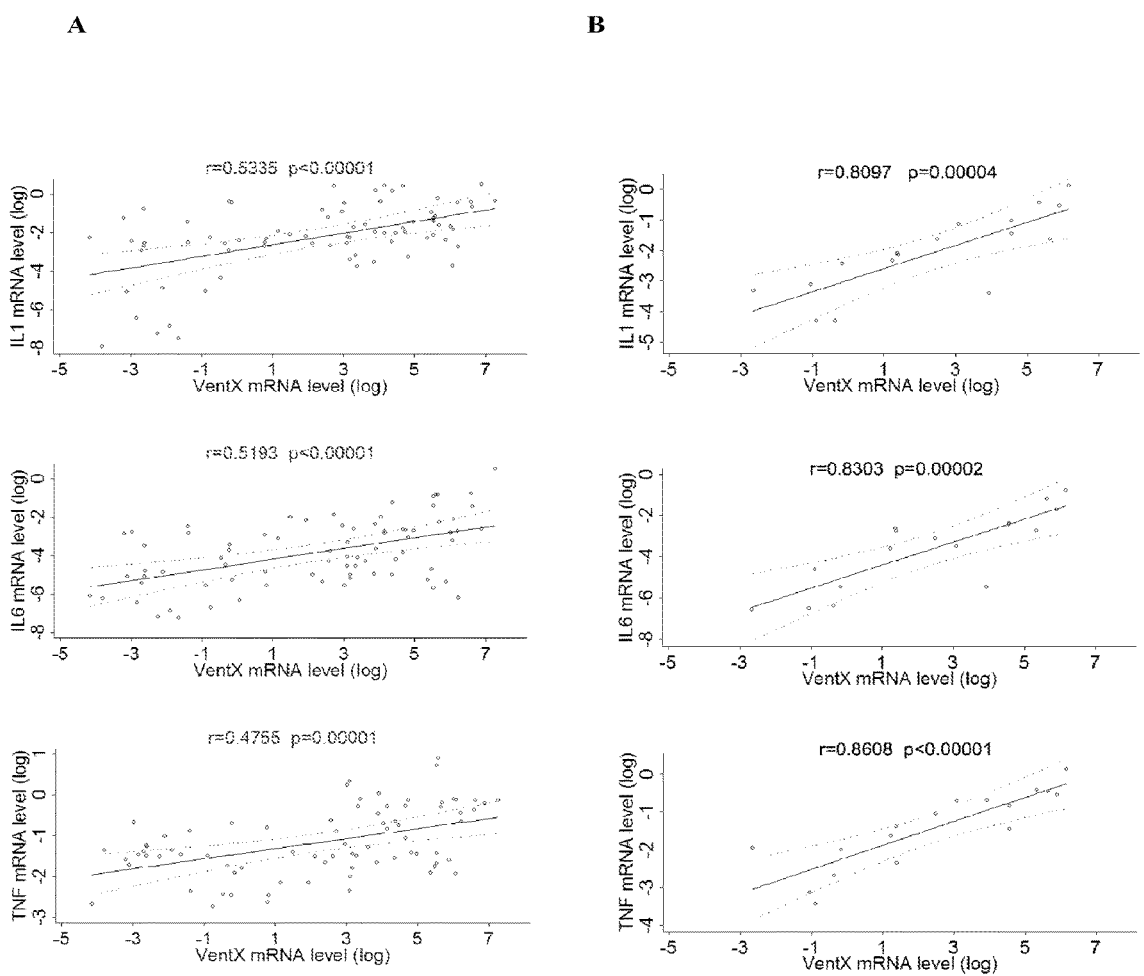
FIG. 11 shows exemplary VentX expression correlation with IL1-β, IL6 and TNF-α levels in SLE/RA patients. (A) Total RNA was isolated from peripheral blood leukocytes of SLE/RA patients. Quantitative measurements of mRNA levels of VentX and the indicated cytokines were performed as described in materials and methods. Scatter distributions and regression lines (solid line) of the mRNA levels of IL1-β, IL6 and TNF-α were plotted against VentX mRNA level from all patients. Confidence intervals of 99% were indicated by the dashed arcs. The regression coefficients (r) were highly statistically significant as indicated. (B) Total RNA was purified from peripheral monocytes of SLE/RA patients. Scatter distributions and regression lines were plotted as above.

Expression of VentX and Pro-Inflammatory Cytokines Correlates in Clinical Patients The findings that VentX controls pro-inflammatory responses in U937 cells (FIG. 5) and primary macrophages (FIG. 8) prompted the determination the potential clinical relevance of these findings, for example, in regards to autoimmune diseases, such as systemic lupus erythematosus (SLE) and rheumatoid arthritis (RA). Previous studies have shown that expression of pro-inflammatory cytokines such as TNF-α, IL1-β and IL6 is often elevated in these patients and that expression levels of pro-inflammatory cytokines are usually associated with disease severity. (Asanuma, et al. 2006 *J Rheumatol* 33:539-545; Sabry, et al. 2006 *Cytokine* 35:148-153; Aringer, et al. 2004 *Lupus* 13:344-347; Davas, et al. 1999 *Clin Rheumatol* 18:17-22.) To assay for a potential relationship between VentX expression and the expression of pro-inflammatory cytokines in clinical setting, the expression level of TNF-α, ILA-β, IL6 and VentX from peripheral blood leukocytes of SLE/RA patients was quantitatively measured. Linear regression analysis of the expression of TNF-α, IL1-β and IL6 against VentX was then performed. As shown in FIG. 11A, VentX expression strongly correlated with the expression of TNF-α, IL1-β and IL6. Similar results were also obtained when purified monocytes from SLE/RA patients were used for the analysis (FIG. 11B), suggesting a regulatory role of VentX in the expression of pro-inflammatory cytokines in SLE/RA patients.

Figure 23:
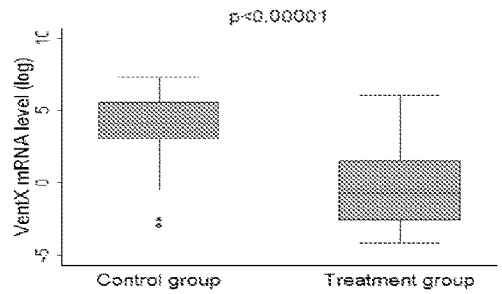
FIG. 23 shows that VentX expression is down-regulated in SLE/RA patients upon immunosuppressant treatment. SLE/RA patients receiving immunosuppressant such as Imuran, Methotrexate or Prednisone were classified as treatment group, while patients not receiving immunosuppressant were classified as control group. (A) Total RNA was isolated from peripheral blood leukocytes of SLE/RA patients. Quantitative measurements of mRNA levels of VentX and the indicated cytokines were performed as described in Materials and Methods. mRNA levels were represented in box plots indicating the median and the lower and upper quartiles. Statistically, significant differences between the immunosuppressant-receiving group and the control group were revealed by Wilcoxon rank-sum test. (B) Total RNA was purified from peripheral monocytes of SLE/RA patients and same analysis was performed as above.
Figure 23:
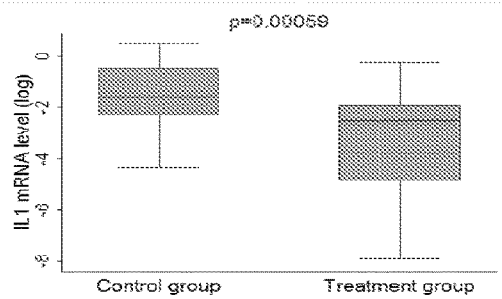
Figure 23:
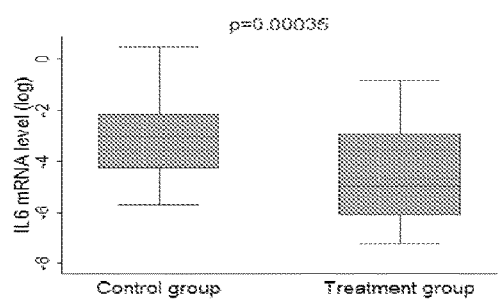
Figure 23:
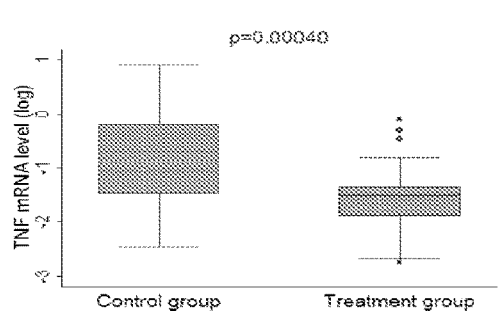
Figure 23:
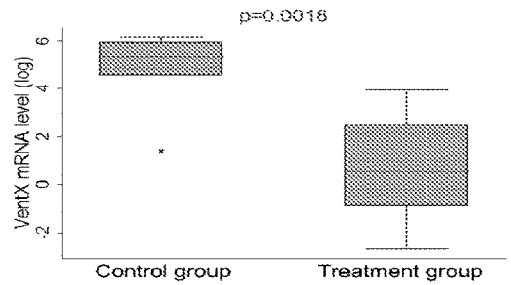
Figure 23:
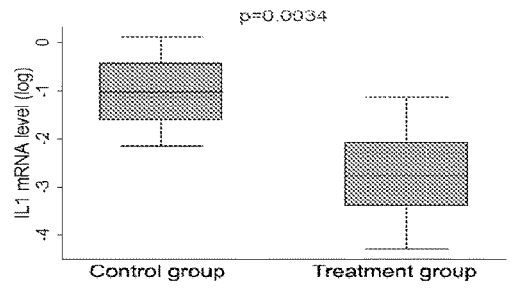
Figure 23:
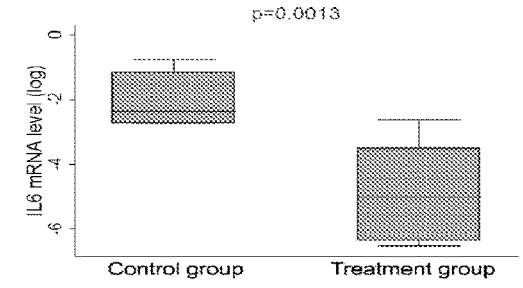
Figure 23:
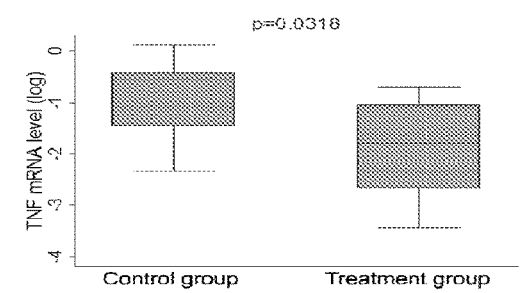

Immunosuppressants remain as a main therapeutic modality to control inflammation in SLE/RA patients. To determine whether VentX may serve as a therapeutic target of immunosuppressant treatment, the SLE/RA patients were divided into two subgroups: those on immunosuppressant and those on non-immunosuppressant regiments. As shown in FIG. 23, VentX expression was significantly down-regulated in SLE/RA patients receiving immunosuppressants (treatment group) in comparison with that of the control group. Furthermore, expression levels of TNF-α, IL1-β and IL6 are also decreased in patients receiving immunosuppressant treatment (FIG. 23).

Experimental

Monocytes Isolation and Culture

Peripheral blood mononuclear cells (PBMC) from healthy adult donors at Children's Hospital Boston were isolated by Ficoll density gradient centrifugation. Experiments with human materials were performed in accordance with guidelines approved by the institutional review committee of Brigham and Women's Hospital. CD14$^+$ monocytes were purified from PBMCs using anti-CD14-coated microbeads (Miltenyi Biotec). The purity of freshly isolated CD14$^+$ monocytes was more than 95% as analyzed by flow cytometry. Monocytes were cultured in 12-well plates at $1\times10^6$ cells/ml with RPMI 1640 medium containing 10% fetal bovine serum (FBS). M-CSF, GM-CSF, and IL3 were purchased from PeproTech and used at the final concentration of 100 ng/ml. Cytokines were added to cultures every 2 or 3 days.

RNA Interference

Human primary monocytes were transfected using the Human Monocyte Nucleofector Kit (Lonza) according to the manufacturer's instructions. Briefly, $5\times10^6$ monocytes were resuspended into 100 μl nucleofector solution with 0.5 nmol of either VentX siRNA (forward: 5'-UUCAGAAUCGCCG- CAUGAAACACAAACGG-3' (SEQ ID NO:4); reverse: 5'-CCGUUUGUGUUUCAUGCGGCGAUUCUGAA-3' (SEQ ID NO:5)) or non-effective GFP siRNA (forward: 5'-UGACCACCCUGACCUACGGCGUGCAGUGC-3' (SEQ ID NO:6); 5'-reverse: GCACUGCACGCCGUAG-GUCAGGGUGGUCA-3' (SEQ ID NO:7)) before electroporation with nucleofector II Device (Lonza). Cells were then immediately removed from the device and incubated overnight with 1 ml pre-warmed Human Monocyte Nucleofector Medium containing 2 mM glutamine and 10% FBS. Cells were then resuspended into complete RPMI medium and treated with appropriate cytokines to induce differentiation into macrophages. Similarly, macrophages derived from monocytes were transfected with Human Macrophage Nucleofector Kit (Lonza) following the manufacturer's instructions.

Generation of U937 Cell Line Conditionally Expressing VentX

Human promonocytic cell line U937 was obtained from American Type Culture Collection (ATCC). Plasmid constructs expressing VentX have been described previously (20). GFP.VentX fusion fragment was cut from pCS2 expression vector through digestion with BamHI/SnaBI and subcloned into pRetroX-Tight-Puro retroviral vector (Retro-X™ Tet-On Advanced Expression System, Clontech) digested with BamHI/NruI. Retroviruses were packaged through co-transfection of pCL-Ampho packaging vector (IMGENEX) and retroviral vectors into HEK293 cells. A U937 cell line conditionally expressing GFP.VentX was generated through co-transduction of pRetroX-GFP.VentX and pRetroX-Tet-On Advanced retroviruses. GFP.VentX positive cells were sorted by FACSAria high-speed sorter (BD Bioscience) after incubation with 1.0 µg/ml doxycycline for 24 hours (Dana-Farber Cancer Institute Flow Cytometry Core Facility). Sorted cells were then maintained in RPMI 1640 medium in the absence of doxycycline. A U937 cell line conditionally expressing GFP was similarly generated for comparison.

FACS Analysis

Phenotypic analysis of monocytes/macrophages was performed using flow cytometry after immunolabeling of cells with fluorescence dye conjugated antibodies. The following antibodies were used: PE-conjugated anti-CD71, CD11b, CD11c, CD16, CD64, CD80, CD86, HLA-DR, CD14, TLR4, IL1-β and TNF-α, and FITC-conjugated anti-CD40, CD36 (eBioscience); FITC-conjugated anti-mannose receptor (MR), and unconjugated mouse anti-MCSFR (R & D Systems). Isotype control labeling was performed in parallel. Antibodies were diluted as recommended by the supplier. PE-conjugated rabbit against mouse IgG antibody was used for secondary M-CSFR staining Labeled cells were analyzed with FACScan flow cytometer (BD Bioscience) using CellQuest software. Results are expressed as the percentage of positive cells and/or mean fluorescence intensity (MFI) values after subtraction of the MFI obtained with the isotype control antibody.

Western Blot

Cells were lysed in solution A (50 mM Tris-HCl, pH 7.8, 420 mM NaCl, 1 mM EDTA, 0.5% Nonidet P-40, 0.34 M sucrose, 10% glycerol, 1 mM $Na_3VO_4$, 10 mM NaF and β-glycerophosphate, 1 mM PMSF, and protease inhibitor cocktail) as described previously (64). Proteins resolved by SDS-PAGE were transferred onto PVDF membrane, which were detected with optimal dilutions of primary antibodies, followed by horseradish peroxidase-linked secondary antibodies. Primary antibodies used were from Cell Signaling except anti-VentX sera.

RT-PCR

Total RNA was isolated by the TRIzol reagent, and an equal amount of RNA was used for first-strand cDNA synthesis with SuperScript III First-Strand Synthesis System (Invitrogen) according to the manufacturer's protocol. To amplify VentX cDNA with conventional PCR, AccuPrime™ Taq DNA polymerase system (Invitrogen) was used following the manufacturer's instructions. PCR products were separated on 2% agarose gels and stained with ethidium bromide. GAPDH was used as an internal control. Quantitative measurement of VentX and cytokines cDNA were performed with SYBR Green on a LightCycler® (480 Real-Time PCR System; Roche). The primers used are listed in the Sequence Listing (SEQ ID NOs: 24-109).

Cytokine Measurements

Levels of IL-1β and TNF-α and IL12p70 in the supernatants of E. coli LPS (Sigma) and IFN-γ (PeproTech) treated macrophage or LPS treated U937 cells were quantified using ELISA kits obtained from eBiosciences. Analyses were conducted according to the manufacturer's instructions.

Phagocytosis Assay

Phagocytosis of cultured monocytes/macrophages or U937 cells were performed with pHrodo™ S. aureus BioParticles® conjugates from Invitrogen. Briefly, S. aureus particles were first sonicated to achieve homogeneous solution and then opsonized for 60 min at 37° C. with opsonizing reagent obtained from Invitrogen (Cat. S-2860). After the S. aureus particles were washed 3 times in PBS, they were resuspended to an appropriate concentration for phagocytosis assay. $5 \times 10^5$ cells were incubated with 100 µl of opsonized particles for 2 hours at 37° C. After extensive washings, cellular phagocytosis of bioparticles was monitored by flow cytometry. Negative controls were also performed in parallel by incubating cells with particles on ice instead of at 37° C.

Detection of Reactive Oxygen Species (ROS) and Nitric Oxide (NO)

The ROS level in activated macrophages was detected with Image-iT® LIVE Green Reactive Oxygen Species Detection Kit (Invitrogen) basically following the manufacturer's instructions except that the results were analyzed by both fluorescence microscope and flow cytometry. The NO level was determined by Griess Reagent Kit for Nitrite Determination (Invitrogen) following the protocol provided by the manufacturer.

Cytostaining

For Wright-Giemsa staining, a staining kit from Sigma was used according to the manufacturer's instructions.

Mixed Lymphocyte Reaction

Macrophages were generated by incubating CD14-beads isolated monocytes with 100 ng/ml M-CSF for 4 days. Macrophages were then transfected with siRNA against VentX or GFP, as described above. After 3 days of transfection, the cells were harvested, washed 3 times in PBS, and irradiated (5000 rad) before incubation with allogenic naive CD4$^+$ T cells ($10^5$/well) for 7 days in 96-well flat-bottom microplates (Costar). Various numbers of irradiated macrophages were added as indicated. The cells were pulsed for the last 18 hours with 1 µCi of [$^3$H] thymidine to determine T cell proliferation.

Luciferase Reporter Assay

The 1.56 kb fragment of M-CSFR promoter region was amplified with forward primer: 5'-GT-TACGCGTGGGAAGCCAAGGTATGAGAATC-3' (SEQ ID NO:8), and reverse primer: 5'-AAGCTCGAGCCTCG-GTGGGGAAGTGGCAG-3' (SEQ ID NO:9). The 2.8 kb fragment of VentX promoter region was amplified with forward primer: 5'-CAGCCGAGTCTCACTCTGTC-3' (SEQ ID NO:1), and reverse primer: 5'-CAAAGCTGGA-GAGCTGCTGC-3' (SEQ ID NO:2). The PCR product was subsequently cloned into pGL3 luciferase reporter. 500 ng reporter plasmid with 500 ng of pcDNA-VentX plasmid or empty pcDNA vector were transfected into U937 cells or primary monocytes through electroporation. 10 ng Renilla luciferase plasmid was included for each transfection to normalize reporter activity. Cells were harvested at 48 hours after transfection and analyzed with Dual-Luciferase Reporter Assay System (Promega).

Gel Shift Assay

VentX protein was generated with a in vitro translation kit (TNT® Coupled Reticulocyte Lysate Systems, Promega). The pCS2-VentX plasmid with SP6 promoter was used as template and translated VentX protein was verified by western blot analysis. Gel shift assay was performed with a fluorescence-based Electrophoretic Mobility Shift Assay (EMSA) Kit from Invitrogen following the manufacturer's instruction. The following double-stranded oligonucleotides were used in the experiments: 5'-CTGCGTCTCTAAAATAATAATAATAAATTTT-TAAAAGATATGC-3'(SEQ ID NO:12)(wild type M-CSFR probe, putative homeodomain binding sequence is in bold and underlined); 5'-CT-GCGTCTCTAAAATAAGAAGAATAAATTTT-TAAAAGATATGC-3'(mutant M-CSFR)(SEQ ID NO:13).

ChIP Assay

U937 cell lines conditionally expressing GFP or GFP. VentX were employed to detect the potential interaction of VentX with M-CSFR, Stat1 and JunB promoters. Cells were treated with 1.0 µg/ml doxycycline for 2 days and harvested for chromatin immunoprecipitation (ChIP) assay. The ChIP procedure was performed with a kit from Upstate Biotechnology (Billerica, MA) following the manufacturer's instructions. The GFP antibody (Santa Cruz Biotechnology) was used for the immunoprecipitation. M-CSFR promoter region containing a putative homeodomain binding site was amplified with specific primers: 5'-TAGAGATAACGTCA-GATCTCAC-3' (SEQ ID NO:14) and 5'-CAAAGA-GAAGTTAGGTTGCATG-3' (SEQ ID NO:15); the STAT1 promoter was amplified with primers: 5'-TGACTGATG-GAAAGGGGTGG-3' (SEQ ID NO:16) and 5'-GCCACCT-GTTCTTGGGAGAT-3' (SEQ ID NO:17); the JunB promoter was amplified with primers: 5'-GCTTACTAGCTTTCTGCATA-3' (SEQ ID NO :18) and 5'-GGAGGGGAGAGATCAAAAGG-3' (SEQ ID NO:19); the constant region of immunoglobulin M heavy chain gene (Cµ), which serves as a negative control, was amplified with the following primers: 5'-AACCCTTTTCCCCCTCGTCT-3' (SEQ ID NO:20) and 5'-AGCACCTGTGAGGTG-GCTGC-3' (SEQ ID NO:21). To detect if VentX competes with Foxp1 to bind to M-CSFR promoter region, U937 cells were treated with 1.0 µg/ml doxycycline for 2 days as described above, or primary monocytes were transfected by electroporation with siGFP or siVentX. Cell lysates were then immunoprecipitated with Foxp 1 antibody (Cell signaling) and the M-CSFR promoter region containing the Foxp 1 binding site was amplified with primers: 5'-GCTT-TAGAAGGGCCCCAAAC-3' (SEQ ID NO:22) and 5'-CTACTAGCTCCGCAGGGATC-3' (SEQ ID NO:23). All PCR products were separated on 8% polyacrylamide gel and visualized by ethidium bromide staining. ps Statistical Analysis Data were analyzed using the paired Student's t test (2-tailed) and Wilcoxon rank-sum test. The differences with p value <0.05 were considered statistically significant.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance which can be adapted to the practice of this invention in its various embodiments and equivalents thereof.

Sequence listings and related materials in the ASCII text file named "ZLZ-001US_SEQ-2017-0614_ST25.txt" and created on Jun. 14, 2017 with a size of about 28 kilobytes, is hereby incorporated by reference.

What is claimed is:

1. A method for identifying a compound which regulates VentX expression, the method comprising:
   (a) providing a cell that contains an exogenous reporter gene operably linked to a VentX promoter, the VentX promoter being 2.8 KB in length cloned with the primers: 5'-CAGCCGAGTCTCACTCTGTC-3' (SEQ ID NO: 1) and 5'-CAAAGCTGGAGAGCTGCTGC-3' (SEQ ID NO: 2);
   (b) contacting the cell with a candidate compound; and
   (c) measuring the reporter gene activity,
   wherein the VentX promoter is active in the cell and the candidate compound is a regulator of VentX expression if the measured reporter gene activity is modulated as compared to a baseline activity of the reporter gene measured in the absence of the candidate compound.

2. The method of claim 1, wherein the exogenous reporter gene is a luciferase gene.

3. The method of claim 1, wherein the candidate compound is a small molecule agent.

4. The method of claim 1, wherein the candidate compound is a polypeptide.

5. The method of claim 1, wherein the candidate compound is an oligonucleotide.

* * * * *

SEQUENCE LISTING

```
<160> NUMBER OF SEQ ID NOS: 112

<210> SEQ ID NO 1
<211> LENGTH: 20
<212> TYPE: DNA
<213> ORGANISM: Artificial
<220> FEATURE:
<223> OTHER INFORMATION: primer for cloning VentX promoter

<400> SEQUENCE: 1
cagccgagtc tcactctgtc                                             20

<210> SEQ ID NO 2
<211> LENGTH: 20
<212> TYPE: DNA
<213> ORGANISM: Artificial
<220> FEATURE:
```

```
<223> OTHER INFORMATION: Primer for cloning VentX promoter

<400> SEQUENCE: 2
caaagctgga gagctgctgc                                          20

<210> SEQ ID NO 3
<211> LENGTH: 29
<212> TYPE: RNA
<213> ORGANISM: Artificial
<220> FEATURE:
<223> OTHER INFORMATION: VentX siRNA-2

<400> SEQUENCE: 3
ucuacucaac gucuucuggc cuugccaau                                 29

<210> SEQ ID NO 4
<211> LENGTH: 29
<212> TYPE: RNA
<213> ORGANISM: Artificial
<220> FEATURE:
<223> OTHER INFORMATION: VentX siRNA (forward)

<400> SEQUENCE: 4
uucagaaucg ccgcaugaaa cacaaacgg                                 29

<210> SEQ ID NO 5
<211> LENGTH: 29
<212> TYPE: RNA
<213> ORGANISM: Artificial
<220> FEATURE:
<223> OTHER INFORMATION: VentX siRNA (reverse)

<400> SEQUENCE: 5
ccguuugugu uucaugcggc gauucugaa                                 29

<210> SEQ ID NO 6
<211> LENGTH: 29
<212> TYPE: RNA
<213> ORGANISM: Artificial
<220> FEATURE:
<223> OTHER INFORMATION: GFP siRNA (forward)

<400> SEQUENCE: 6
ugaccacccu gaccuacggc gugcagugc                                 29

<210> SEQ ID NO 7
<211> LENGTH: 29
<212> TYPE: RNA
<213> ORGANISM: Artificial
<220> FEATURE:
<223> OTHER INFORMATION: GFP siRNA (reverse)

<400> SEQUENCE: 7
gcacugcacg ccguagguca ggugguca                                  29

<210> SEQ ID NO 8
<211> LENGTH: 31
<212> TYPE: DNA
<213> ORGANISM: Artificial
<220> FEATURE:
<223> OTHER INFORMATION: forward primer for cloning part of M-CSFR
      promoter region

<400> SEQUENCE: 8
gttacgcgtg ggaagccaag gtatgagaat c                              31
```

<210> SEQ ID NO 9
<211> LENGTH: 29
<212> TYPE: DNA
<213> ORGANISM: Artificial
<220> FEATURE:
<223> OTHER INFORMATION: reverse primer for cloning part of M-CSFR
      promoter region

<400> SEQUENCE: 9
aagctcgagc ctcggtgggg aagtggcag                                    29

<210> SEQ ID NO 10
<211> LENGTH: 15
<212> TYPE: DNA
<213> ORGANISM: Artificial
<220> FEATURE:
<223> OTHER INFORMATION: wild type putative homeodomain binding sequence

<400> SEQUENCE: 10
ataataataa taaat                                                   15

<210> SEQ ID NO 11
<211> LENGTH: 15
<212> TYPE: DNA
<213> ORGANISM: Artificial
<220> FEATURE:
<223> OTHER INFORMATION: Mutant putative homeodomain binding sequence

<400> SEQUENCE: 11
ataagaagaa taaat                                                   15

<210> SEQ ID NO 12
<211> LENGTH: 43
<212> TYPE: DNA
<213> ORGANISM: Artificial
<220> FEATURE:
<223> OTHER INFORMATION: wild type M-CSFR probe

<400> SEQUENCE: 12
ctgcgtctct aaaataataa taataaattt ttaaaagata tgc                    43

<210> SEQ ID NO 13
<211> LENGTH: 43
<212> TYPE: DNA
<213> ORGANISM: Artificial
<220> FEATURE:
<223> OTHER INFORMATION: mutant M-CSFR probe

<400> SEQUENCE: 13
ctgcgtctct aaaataagaa gaataaattt ttaaaagata tgc                    43

<210> SEQ ID NO 14
<211> LENGTH: 22
<212> TYPE: DNA
<213> ORGANISM: Artificial
<220> FEATURE:
<223> OTHER INFORMATION: Primer for cloning M-CSFR promoter region
      containing a putative homeodomain binding site

<400> SEQUENCE: 14
tagagataac gtcagatctc ac                                           22

<210> SEQ ID NO 15
<211> LENGTH: 22
<212> TYPE: DNA
<213> ORGANISM: Artificial

```
<220> FEATURE:
<223> OTHER INFORMATION: Primer for cloning M-CSFR promoter region
      containing a putative homeodomain binding site

<400> SEQUENCE: 15
caaagagaag ttaggttgca tg                                               22

<210> SEQ ID NO 16
<211> LENGTH: 20
<212> TYPE: DNA
<213> ORGANISM: Artificial
<220> FEATURE:
<223> OTHER INFORMATION: primer for cloning STAT1 promoter

<400> SEQUENCE: 16
tgactgatgg aaagggtgg                                                   20

<210> SEQ ID NO 17
<211> LENGTH: 20
<212> TYPE: DNA
<213> ORGANISM: Artificial
<220> FEATURE:
<223> OTHER INFORMATION: primer for cloning STAT1 promoter region

<400> SEQUENCE: 17
gccacctgtt cttgggagat                                                  20

<210> SEQ ID NO 18
<211> LENGTH: 20
<212> TYPE: DNA
<213> ORGANISM: Artificial
<220> FEATURE:
<223> OTHER INFORMATION: primer for cloning JunB promoter region

<400> SEQUENCE: 18
gcttactagc tttctgcata                                                  20

<210> SEQ ID NO 19
<211> LENGTH: 20
<212> TYPE: DNA
<213> ORGANISM: Artificial
<220> FEATURE:
<223> OTHER INFORMATION: primer for cloning JunB promoter region

<400> SEQUENCE: 19 ggagggaga gatcaaaagg                                                   20

<210> SEQ ID NO 20
<211> LENGTH: 20
<212> TYPE: DNA
<213> ORGANISM: Artificial
<220> FEATURE:
<223> OTHER INFORMATION: primer for cloning the constant region of
      immunoglobulin M heavy chain gene

<400> SEQUENCE: 20
aacccttttc cccctcgtct                                                  20

<210> SEQ ID NO 21
<211> LENGTH: 20
<212> TYPE: DNA
<213> ORGANISM: Artificial
<220> FEATURE:
<223> OTHER INFORMATION: primer for cloning the constant region of
      immunoglobulin M heavy chain gene

<400> SEQUENCE: 21
```
agcacctgtg aggtggctgc                                                    20

<210> SEQ ID NO 22
<211> LENGTH: 20
<212> TYPE: DNA
<213> ORGANISM: Artificial
<220> FEATURE:
<223> OTHER INFORMATION: primer for cloning M-CSFR promoter region
      containing the Foxp1 binding site

<400> SEQUENCE: 22
gctttagaag ggccccaaac                                                    20

<210> SEQ ID NO 23
<211> LENGTH: 20
<212> TYPE: DNA
<213> ORGANISM: Artificial
<220> FEATURE:
<223> OTHER INFORMATION: primer for cloning M-CSFR promoter region
      containing the Foxp1 binding site

<400> SEQUENCE: 23
ctactagctc cgcagggatc                                                    20

<210> SEQ ID NO 24
<211> LENGTH: 20
<212> TYPE: DNA
<213> ORGANISM: Artificial
<220> FEATURE:
<223> OTHER INFORMATION: Forward primer for VentX-C

<400> SEQUENCE: 24
aaggcaatta ggcgctgctt                                                    20

<210> SEQ ID NO 25
<211> LENGTH: 21
<212> TYPE: DNA
<213> ORGANISM: Artificial
<220> FEATURE:
<223> OTHER INFORMATION: reverse primer for VentX-C

<400> SEQUENCE: 25
acagaacaac tgagtcctcc a                                                  21

<210> SEQ ID NO 26
<211> LENGTH: 18
<212> TYPE: DNA
<213> ORGANISM: Artificial
<220> FEATURE:
<223> OTHER INFORMATION: forward primer for VentX-R

<400> SEQUENCE: 26
ccgtcagcat caaggagg                                                      18

<210> SEQ ID NO 27
<211> LENGTH: 19
<212> TYPE: DNA
<213> ORGANISM: Artificial
<220> FEATURE:
<223> OTHER INFORMATION: reverse primer for VentX-R

<400> SEQUENCE: 27
ctggacctct gagagctgc                                                     19

<210> SEQ ID NO 28

```
<211> LENGTH: 20
<212> TYPE: DNA
<213> ORGANISM: Artificial
<220> FEATURE:
<223> OTHER INFORMATION: forward primer for IL1B

<400> SEQUENCE: 28
aagctgatgg ccctaaacag                                              20

<210> SEQ ID NO 29
<211> LENGTH: 20
<212> TYPE: DNA
<213> ORGANISM: artificial
<220> FEATURE:
<223> OTHER INFORMATION: reverse primer for IL1B

<400> SEQUENCE: 29
aggtgcatcg tgcacataag                                              20

<210> SEQ ID NO 30
<211> LENGTH: 24
<212> TYPE: DNA
<213> ORGANISM: artificial
<220> FEATURE:
<223> OTHER INFORMATION: forward primer for IL6

<400> SEQUENCE: 30
gaactccttc tccacaagcg cctt                                         24

<210> SEQ ID NO 31
<211> LENGTH: 28
<212> TYPE: DNA
<213> ORGANISM: artificial
<220> FEATURE:
<223> OTHER INFORMATION: reverse primer for IL6

<400> SEQUENCE: 31
caaaagacca gtgatgattt tcaccagg                                     28

<210> SEQ ID NO 32
<211> LENGTH: 18
<212> TYPE: DNA
<213> ORGANISM: Artificial
<220> FEATURE:
<223> OTHER INFORMATION: forward primer for TNFa

<400> SEQUENCE: 32
cgccaccacg ctcttctg                                                18

<210> SEQ ID NO 33
<211> LENGTH: 18
<212> TYPE: DNA
<213> ORGANISM: artificial
<220> FEATURE:
<223> OTHER INFORMATION: reverse primer for TNFa

<400> SEQUENCE: 33
gccattggcc aggagggc                                                18

<210> SEQ ID NO 34
<211> LENGTH: 20
<212> TYPE: DNA
<213> ORGANISM: artificial
<220> FEATURE:
<223> OTHER INFORMATION: forward primer for IL8

<400> SEQUENCE: 34
```
atgacttcca agctggccgt                                               20

<210> SEQ ID NO 35
<211> LENGTH: 22
<212> TYPE: DNA
<213> ORGANISM: Artificial
<220> FEATURE:
<223> OTHER INFORMATION: reverse primer for IL8

<400> SEQUENCE: 35
cctcttcaaa aacttctcca ca                                            22

<210> SEQ ID NO 36
<211> LENGTH: 21
<212> TYPE: DNA
<213> ORGANISM: ARTIFICIAL
<220> FEATURE:
<223> OTHER INFORMATION: forwrad primer for M-CSF

<400> SEQUENCE: 36
gtactgtagc cacatgattg g                                             21

<210> SEQ ID NO 37
<211> LENGTH: 21
<212> TYPE: DNA
<213> ORGANISM: artificial
<220> FEATURE:
<223> OTHER INFORMATION: reverse primer for M-CSF

<400> SEQUENCE: 37
ctggagcatt cagcaaagct g                                             21

<210> SEQ ID NO 38
<211> LENGTH: 22
<212> TYPE: DNA
<213> ORGANISM: artificial
<220> FEATURE:
<223> OTHER INFORMATION: forward primer for M-CSFR

<400> SEQUENCE: 38
cggtgcagag cctgctgact gt                                            22

<210> SEQ ID NO 39
<211> LENGTH: 22
<212> TYPE: DNA
<213> ORGANISM: artificial
<220> FEATURE:
<223> OTHER INFORMATION: reverse primer for M-CSFR

<400> SEQUENCE: 39
acaggctccc agaaggttga cg                                            22

<210> SEQ ID NO 40
<211> LENGTH: 19
<212> TYPE: DNA
<213> ORGANISM: artificial
<220> FEATURE:
<223> OTHER INFORMATION: primer for IL12p35

<400> SEQUENCE: 40
gcgcgcagcc tcctccttg                                                19

<210> SEQ ID NO 41
<211> LENGTH: 20
<212> TYPE: DNA

<213> ORGANISM: artificial
<220> FEATURE:
<223> OTHER INFORMATION: primer for IL12p35

<400> SEQUENCE: 41
tggaggccag gcaactccca                                               20

<210> SEQ ID NO 42
<211> LENGTH: 22
<212> TYPE: DNA
<213> ORGANISM: artificial
<220> FEATURE:
<223> OTHER INFORMATION: primer for IL12p40

<400> SEQUENCE: 42
gcagaggctc ttctgacccc ca                                            22

<210> SEQ ID NO 43
<211> LENGTH: 20
<212> TYPE: DNA
<213> ORGANISM: artificial
<220> FEATURE:
<223> OTHER INFORMATION: primer for IL12p40

<400> SEQUENCE: 43
agctgacctc cacctgccga                                               20

<210> SEQ ID NO 44
<211> LENGTH: 20
<212> TYPE: DNA
<213> ORGANISM: artificial
<220> FEATURE:
<223> OTHER INFORMATION: primer for TLR4

<400> SEQUENCE: 44
aagccgaaag gtgattgttg                                               20

<210> SEQ ID NO 45
<211> LENGTH: 20
<212> TYPE: DNA
<213> ORGANISM: artificial
<220> FEATURE:
<223> OTHER INFORMATION: primer for TLR4

<400> SEQUENCE: 45
ctgagcaggg tcttctccac                                               20

<210> SEQ ID NO 46
<211> LENGTH: 20
<212> TYPE: DNA
<213> ORGANISM: artificial
<220> FEATURE:
<223> OTHER INFORMATION: primer for CD14

<400> SEQUENCE: 46
cgcaacacag gaatggagac                                               20

<210> SEQ ID NO 47
<211> LENGTH: 20
<212> TYPE: DNA
<213> ORGANISM: Artificial
<220> FEATURE:
<223> OTHER INFORMATION: primer for CD14

<400> SEQUENCE: 47
ccagcgaacg acagattgag                                               20

<210> SEQ ID NO 48
<211> LENGTH: 20
<212> TYPE: DNA
<213> ORGANISM: artificial
<220> FEATURE:
<223> OTHER INFORMATION: primer for MD-2

<400> SEQUENCE: 48
gaatcttcca aagcgcaaag                                              20

<210> SEQ ID NO 49
<211> LENGTH: 20
<212> TYPE: DNA
<213> ORGANISM: artificial
<220> FEATURE:
<223> OTHER INFORMATION: primer for MD-2

<400> SEQUENCE: 49
aggatgacaa actccaagca                                              20

<210> SEQ ID NO 50
<211> LENGTH: 22
<212> TYPE: DNA
<213> ORGANISM: artificial
<220> FEATURE:
<223> OTHER INFORMATION: primer for IFNGR1

<400> SEQUENCE: 50
catcacgtca taccagccat tt                                           22

<210> SEQ ID NO 51
<211> LENGTH: 22
<212> TYPE: DNA
<213> ORGANISM: artificial
<220> FEATURE:
<223> OTHER INFORMATION: primer for IFNGR1

<400> SEQUENCE: 51
ctggattgtc ttcggtatgc at                                           22

<210> SEQ ID NO 52
<211> LENGTH: 26
<212> TYPE: DNA
<213> ORGANISM: artificial
<220> FEATURE:
<223> OTHER INFORMATION: primer for IFNGR2

<400> SEQUENCE: 52
caaggacagc tcaccaaagg atgacg                                       26

<210> SEQ ID NO 53
<211> LENGTH: 26
<212> TYPE: DNA
<213> ORGANISM: artificial
<220> FEATURE:
<223> OTHER INFORMATION: primer for IFNGR2

<400> SEQUENCE: 53
cagctccgat ggcttgatct cttcca                                       26

<210> SEQ ID NO 54
<211> LENGTH: 22
<212> TYPE: DNA
<213> ORGANISM: artificial
<220> FEATURE:

```
<223> OTHER INFORMATION: primer for JunB

<400> SEQUENCE: 54
atggaacagc ccttctacca cg                                        22

<210> SEQ ID NO 55
<211> LENGTH: 21
<212> TYPE: DNA
<213> ORGANISM: artificial
<220> FEATURE:
<223> OTHER INFORMATION: primer for JunB

<400> SEQUENCE: 55
aggctcggtt tcaggagttt g                                         21

<210> SEQ ID NO 56
<211> LENGTH: 23
<212> TYPE: DNA
<213> ORGANISM: artificial
<220> FEATURE:
<223> OTHER INFORMATION: primer for JunD

<400> SEQUENCE: 56
gtctacgcga acctgagcag cta                                       23

<210> SEQ ID NO 57
<211> LENGTH: 23
<212> TYPE: DNA
<213> ORGANISM: artificial
<220> FEATURE:
<223> OTHER INFORMATION: primer for JunD

<400> SEQUENCE: 57
ctcgtccttg agcgcagcca ggc                                       23

<210> SEQ ID NO 58
<211> LENGTH: 19
<212> TYPE: DNA
<213> ORGANISM: artificial
<220> FEATURE:
<223> OTHER INFORMATION: primer for c-Jun

<400> SEQUENCE: 58
tcgacatgga gtcccagga                                            19

<210> SEQ ID NO 59
<211> LENGTH: 20
<212> TYPE: DNA
<213> ORGANISM: artificial
<220> FEATURE:
<223> OTHER INFORMATION: primer for c-Jun

<400> SEQUENCE: 59
ggcgattctc tccagcttcc                                           20

<210> SEQ ID NO 60
<211> LENGTH: 22
<212> TYPE: DNA
<213> ORGANISM: artificial
<220> FEATURE:
<223> OTHER INFORMATION: primer for c-Fos

<400> SEQUENCE: 60
tgcctctcct caatgaccct ga                                        22
```

```
<210> SEQ ID NO 61
<211> LENGTH: 22
<212> TYPE: DNA
<213> ORGANISM: artificial
<220> FEATURE:
<223> OTHER INFORMATION: primer for c-Fos

<400> SEQUENCE: 61
ataggtccat gtctggcacg ga                                              22

<210> SEQ ID NO 62
<211> LENGTH: 20
<212> TYPE: DNA
<213> ORGANISM: artificial
<220> FEATURE:
<223> OTHER INFORMATION: primer for fosB

<400> SEQUENCE: 62
agcagcagct aaatgcagga                                                 20

<210> SEQ ID NO 63
<211> LENGTH: 19
<212> TYPE: DNA
<213> ORGANISM: artificial
<220> FEATURE:
<223> OTHER INFORMATION: primer for fosB

<400> SEQUENCE: 63
ttttggagct cggcgatct                                                  19

<210> SEQ ID NO 64
<211> LENGTH: 20
<212> TYPE: DNA
<213> ORGANISM: artificial
<220> FEATURE:
<223> OTHER INFORMATION: primer for RelA

<400> SEQUENCE: 64
gaagaagagt cctttcagcg                                                 20

<210> SEQ ID NO 65
<211> LENGTH: 20
<212> TYPE: DNA
<213> ORGANISM: artificial
<220> FEATURE:
<223> OTHER INFORMATION: primer for RelA

<400> SEQUENCE: 65
gggaggacgt aaagggatag                                                 20

<210> SEQ ID NO 66
<211> LENGTH: 20
<212> TYPE: DNA
<213> ORGANISM: artificial
<220> FEATURE:
<223> OTHER INFORMATION: primer for RelB

<400> SEQUENCE: 66
gcagcgagcc attgcctttc                                                 20

<210> SEQ ID NO 67
<211> LENGTH: 22
<212> TYPE: DNA
<213> ORGANISM: artificial
<220> FEATURE:
<223> OTHER INFORMATION: primer for RelB
```

```
<400> SEQUENCE: 67
ggtccagcat ggtgaagagt gt                                              22

<210> SEQ ID NO 68
<211> LENGTH: 22
<212> TYPE: DNA
<213> ORGANISM: artificial
<220> FEATURE:
<223> OTHER INFORMATION: primer for c-Rel

<400> SEQUENCE: 68
cgaacccaat ttatgacaac cg                                              22

<210> SEQ ID NO 69
<211> LENGTH: 24
<212> TYPE: DNA
<213> ORGANISM: artificial
<220> FEATURE:
<223> OTHER INFORMATION: primer for c-Rel

<400> SEQUENCE: 69
ttttgtttct ttgctttatt gccg                                            24

<210> SEQ ID NO 70
<211> LENGTH: 20
<212> TYPE: DNA
<213> ORGANISM: artificial
<220> FEATURE:
<223> OTHER INFORMATION: primer for NFkB1

<400> SEQUENCE: 70
tccacaaggc agcaaataga                                                 20

<210> SEQ ID NO 71
<211> LENGTH: 20
<212> TYPE: DNA
<213> ORGANISM: artificial
<220> FEATURE:
<223> OTHER INFORMATION: primer for NFkB1

<400> SEQUENCE: 71 ggggcattttt gttgagagtt                                                20

<210> SEQ ID NO 72
<211> LENGTH: 19
<212> TYPE: DNA
<213> ORGANISM: artificial
<220> FEATURE:
<223> OTHER INFORMATION: primer for NFkB2

<400> SEQUENCE: 72
ttctgaaggc tggtctgac                                                  19

<210> SEQ ID NO 73
<211> LENGTH: 20
<212> TYPE: DNA
<213> ORGANISM: artificial
<220> FEATURE:
<223> OTHER INFORMATION: primer for NFkB2

<400> SEQUENCE: 73
agtgaggtca agaggcgtgt                                                 20

<210> SEQ ID NO 74
<211> LENGTH: 20
```

```
<212> TYPE: DNA
<213> ORGANISM: artificial
<220> FEATURE:
<223> OTHER INFORMATION: primer for B-actin

<400> SEQUENCE: 74
gcaaagacct gtacgccaac                                            20

<210> SEQ ID NO 75
<211> LENGTH: 20
<212> TYPE: DNA
<213> ORGANISM: artificial
<220> FEATURE:
<223> OTHER INFORMATION: primer for B-actin

<400> SEQUENCE: 75
ctagaagcat ttgcggtgga                                            20

<210> SEQ ID NO 76
<211> LENGTH: 25
<212> TYPE: DNA
<213> ORGANISM: artificial
<220> FEATURE:
<223> OTHER INFORMATION: primer for CD163

<400> SEQUENCE: 76
acatagatca tgcatctgtc atttg                                      25

<210> SEQ ID NO 77
<211> LENGTH: 25
<212> TYPE: DNA
<213> ORGANISM: artificial
<220> FEATURE:
<223> OTHER INFORMATION: primer for CD163

<400> SEQUENCE: 77
cattctcctt ggaatctcac ttcta                                      25

<210> SEQ ID NO 78
<211> LENGTH: 20
<212> TYPE: DNA
<213> ORGANISM: artificial
<220> FEATURE:
<223> OTHER INFORMATION: primer for CCL18

<400> SEQUENCE: 78
agctctgctg cctcgtctat                                            20

<210> SEQ ID NO 79
<211> LENGTH: 20
<212> TYPE: DNA
<213> ORGANISM: artificial
<220> FEATURE:
<223> OTHER INFORMATION: primer for CCL18

<400> SEQUENCE: 79
cccacttctt attggggtca                                            20

<210> SEQ ID NO 80
<211> LENGTH: 22
<212> TYPE: DNA
<213> ORGANISM: artificial
<220> FEATURE:
<223> OTHER INFORMATION: primer for IL10

<400> SEQUENCE: 80
```
gatccagttt tacctggagg ag                                          22

<210> SEQ ID NO 81
<211> LENGTH: 21
<212> TYPE: DNA
<213> ORGANISM: artificial
<220> FEATURE:
<223> OTHER INFORMATION: primer for IL10

<400> SEQUENCE: 81
cctgagggtc ttcaggttct c                                           21

<210> SEQ ID NO 82
<211> LENGTH: 22
<212> TYPE: DNA
<213> ORGANISM: artificial
<220> FEATURE:
<223> OTHER INFORMATION: primer for MR

<400> SEQUENCE: 82
cgaggaagag gttcggttca cc                                          22

<210> SEQ ID NO 83
<211> LENGTH: 20
<212> TYPE: DNA
<213> ORGANISM: artificial
<220> FEATURE:
<223> OTHER INFORMATION: primer for MR

<400> SEQUENCE: 83
gcaatcccgg ttctcatggc                                             20

<210> SEQ ID NO 84
<211> LENGTH: 20
<212> TYPE: DNA
<213> ORGANISM: artificial
<220> FEATURE:
<223> OTHER INFORMATION: primer for p21

<400> SEQUENCE: 84
aaactttgga gtcccctcac                                             20

<210> SEQ ID NO 85
<211> LENGTH: 20
<212> TYPE: DNA
<213> ORGANISM: artificial
<220> FEATURE:
<223> OTHER INFORMATION: primer for p21

<400> SEQUENCE: 85
aaaggctcaa cactgagacg                                             20

<210> SEQ ID NO 86
<211> LENGTH: 20
<212> TYPE: DNA
<213> ORGANISM: artificial
<220> FEATURE:
<223> OTHER INFORMATION: primer for AML1

<400> SEQUENCE: 86
acagagacat tgccaaccat                                             20

<210> SEQ ID NO 87
<211> LENGTH: 20
<212> TYPE: DNA
<213> ORGANISM: artificial

```
<220> FEATURE:
<223> OTHER INFORMATION: primer for AML1

<400> SEQUENCE: 87
caggacattt gagtggaacc                                                 20

<210> SEQ ID NO 88
<211> LENGTH: 20
<212> TYPE: DNA
<213> ORGANISM: artificial
<220> FEATURE:
<223> OTHER INFORMATION: primer for Foxp1

<400> SEQUENCE: 88
agatattgcg cagaaccaag                                                 20

<210> SEQ ID NO 89
<211> LENGTH: 20
<212> TYPE: DNA
<213> ORGANISM: artificial
<220> FEATURE:
<223> OTHER INFORMATION: primer for Foxp1

<400> SEQUENCE: 89
cgcacaaaac acttgtgaag                                                 20

<210> SEQ ID NO 90
<211> LENGTH: 20
<212> TYPE: DNA
<213> ORGANISM: artificial
<220> FEATURE:
<223> OTHER INFORMATION: primer for C/EBPa

<400> SEQUENCE: 90
ctaggaacac gaagcacgat                                                 20

<210> SEQ ID NO 91
<211> LENGTH: 20
<212> TYPE: DNA
<213> ORGANISM: artificial
<220> FEATURE:
<223> OTHER INFORMATION: primer for C/EBPa

<400> SEQUENCE: 91
atggtggttt agcagagacg                                                 20

<210> SEQ ID NO 92
<211> LENGTH: 20
<212> TYPE: DNA
<213> ORGANISM: artificial
<220> FEATURE:
<223> OTHER INFORMATION: primer for Egr-1

<400> SEQUENCE: 92
tgaccgcaga gtcttttcct                                                 20

<210> SEQ ID NO 93
<211> LENGTH: 20
<212> TYPE: DNA
<213> ORGANISM: artificial
<220> FEATURE:
<223> OTHER INFORMATION: primer for Egr-1

<400> SEQUENCE: 93
tgggttggtc atgctcacta                                                 20
```

<210> SEQ ID NO 94
<211> LENGTH: 20
<212> TYPE: DNA
<213> ORGANISM: artificial
<220> FEATURE:
<223> OTHER INFORMATION: primer for HIF-1

<400> SEQUENCE: 94
gctgatttgt gaacccattc					20

<210> SEQ ID NO 95
<211> LENGTH: 20
<212> TYPE: DNA
<213> ORGANISM: artificial
<220> FEATURE:
<223> OTHER INFORMATION: primer for HIF-1

<400> SEQUENCE: 95
aaattgagcg gcctaaaagt					20

<210> SEQ ID NO 96
<211> LENGTH: 20
<212> TYPE: DNA
<213> ORGANISM: artificial
<220> FEATURE:
<223> OTHER INFORMATION: primer for Stat6

<400> SEQUENCE: 96
ctagaggcca gggatagagg					20

<210> SEQ ID NO 97
<211> LENGTH: 20
<212> TYPE: DNA
<213> ORGANISM: artificial
<220> FEATURE:
<223> OTHER INFORMATION: primer for Stat6

<400> SEQUENCE: 97
cagcccttgt acttttgcat					20

<210> SEQ ID NO 98
<211> LENGTH: 20
<212> TYPE: DNA
<213> ORGANISM: artificial
<220> FEATURE:
<223> OTHER INFORMATION: primer for MafB

<400> SEQUENCE: 98
gagagacgcc tacaaggtca					20

<210> SEQ ID NO 99
<211> LENGTH: 20
<212> TYPE: DNA
<213> ORGANISM: artificial
<220> FEATURE:
<223> OTHER INFORMATION: primer for MafB

<400> SEQUENCE: 99
ctcgctcaag tcaaacaggt					20

<210> SEQ ID NO 100
<211> LENGTH: 20
<212> TYPE: DNA
<213> ORGANISM: artificial
<220> FEATURE:
<223> OTHER INFORMATION: primer for PU1

<400> SEQUENCE: 100
caaggttccc tcttgtcaga                                               20

<210> SEQ ID NO 101
<211> LENGTH: 20
<212> TYPE: DNA
<213> ORGANISM: artificial
<220> FEATURE:
<223> OTHER INFORMATION: primer for PU1

<400> SEQUENCE: 101 aaagggggcag cagaatagtt                                              20

<210> SEQ ID NO 102
<211> LENGTH: 20
<212> TYPE: DNA
<213> ORGANISM: artificial
<220> FEATURE:
<223> OTHER INFORMATION: primer for KLF2

<400> SEQUENCE: 102
gaaaagacca cgatcctcct                                               20

<210> SEQ ID NO 103
<211> LENGTH: 20
<212> TYPE: DNA
<213> ORGANISM: artificial
<220> FEATURE:
<223> OTHER INFORMATION: primer for KLF2

<400> SEQUENCE: 103
gaaccaggta gcccaaaaat                                               20

<210> SEQ ID NO 104
<211> LENGTH: 20
<212> TYPE: DNA
<213> ORGANISM: artificial
<220> FEATURE:
<223> OTHER INFORMATION: primer for KLF4

<400> SEQUENCE: 104
atatgaccca cactgccaga                                               20

<210> SEQ ID NO 105
<211> LENGTH: 20
<212> TYPE: DNA
<213> ORGANISM: artificial
<220> FEATURE:
<223> OTHER INFORMATION: primer for KLF4

<400> SEQUENCE: 105
ccccttggca ttttgtaagt                                               20

<210> SEQ ID NO 106
<211> LENGTH: 20
<212> TYPE: DNA
<213> ORGANISM: artificial
<220> FEATURE:
<223> OTHER INFORMATION: primer for IRF8

<400> SEQUENCE: 106
ccaggactga tttgggagaa                                               20

<210> SEQ ID NO 107

```
<211> LENGTH: 20
<212> TYPE: DNA
<213> ORGANISM: artificial
<220> FEATURE:
<223> OTHER INFORMATION: primer for IRF8

<400> SEQUENCE: 107
aatggaggca tccacttcct                                              20

<210> SEQ ID NO 108
<211> LENGTH: 21
<212> TYPE: DNA
<213> ORGANISM: artificial
<220> FEATURE:
<223> OTHER INFORMATION: primer for c-Myc

<400> SEQUENCE: 108
cagctgctta gacgctggat t                                            21

<210> SEQ ID NO 109
<211> LENGTH: 21
<212> TYPE: DNA
<213> ORGANISM: artificial
<220> FEATURE:
<223> OTHER INFORMATION: primer for c-Myc

<400> SEQUENCE: 109
gtagaaatac ggctgcaccg a                                            21

<210> SEQ ID NO 110
<211> LENGTH: 258
<212> TYPE: PRT
<213> ORGANISM: homo sapiens

<400> SEQUENCE: 110
```

Met Arg Leu Ser Ser Pro Pro Arg Gly Pro Gln Gln Leu Ser Ser
1               5                   10                  15

Phe Gly Ser Val Asp Trp Leu Ser Gln Ser Ser Cys Ser Gly Pro Thr
            20                  25                  30

His Thr Pro Arg Pro Ala Asp Phe Ser Leu Gly Ser Leu Pro Gly Pro
        35                  40                  45

Gly Gln Thr Ser Gly Ala Arg Glu Pro Pro Gln Ala Val Ser Ile Lys
    50                  55                  60

Glu Ala Ala Gly Ser Ser Asn Leu Pro Ala Pro Glu Arg Thr Met Ala
65                  70                  75                  80

Gly Leu Ser Lys Glu Pro Asn Thr Leu Arg Ala Pro Arg Val Arg Thr
                85                  90                  95

Ala Phe Thr Met Glu Gln Val Arg Thr Leu Glu Gly Val Phe Gln His
            100                 105                 110

His Gln Tyr Leu Ser Pro Leu Glu Arg Lys Arg Leu Ala Arg Glu Met
        115                 120                 125

Gln Leu Ser Glu Val Gln Ile Lys Thr Trp Phe Gln Asn Arg Arg Met
    130                 135                 140

Lys His Lys Arg Gln Met Gln Asp Pro Gln Leu His Ser Pro Phe Ser
145                 150                 155                 160

Gly Ser Leu His Ala Pro Pro Ala Phe Tyr Ser Thr Ser Ser Gly Leu
                165                 170                 175

Ala Asn Gly Leu Gln Leu Leu Cys Pro Trp Ala Pro Leu Ser Gly Pro
            180                 185                 190

Gln Ala Leu Met Leu Pro Pro Gly Ser Phe Trp Gly Leu Cys Gln Val

```
                195                 200                 205
Ala Gln Glu Ala Leu Ala Ser Ala Gly Ala Ser Cys Cys Gly Gln Pro
            210                 215                 220
Leu Ala Ser His Pro Pro Thr Pro Gly Arg Pro Ser Leu Gly Pro Ala
225                 230                 235                 240
Leu Ser Thr Gly Pro Arg Gly Leu Cys Ala Met Pro Gln Thr Gly Asp
                245                 250                 255
Ala Phe

<210> SEQ ID NO 111
<211> LENGTH: 258
<212> TYPE: PRT
<213> ORGANISM: Pan troglodytes

<400> SEQUENCE: 111

Met Arg Leu Ser Ser Ser Pro Pro Arg Gly Arg Gln Gln Leu Ser Ser
1               5                   10                  15
Phe Gly Ser Val Asp Trp Leu Ser Gln Ser Ser Cys Ser Gly Pro Thr
                20                  25                  30
His Thr Pro Arg Pro Ala Asp Phe Ser Leu Gly Ser Leu Pro Gly Pro
            35                  40                  45
Gly Gln Thr Ser Gly Ala Arg Glu Pro Pro Gln Ala Val Ser Ile Lys
        50                  55                  60
Glu Ala Ala Arg Ser Ser Asn Leu Pro Ala Pro Glu Arg Thr Val Ala
65                  70                  75                  80
Gly Leu Ser Lys Glu Pro Asn Thr Leu Arg Val Pro Arg Val Arg Thr
                85                  90                  95
Ala Phe Thr Met Glu Gln Val Arg Thr Leu Glu Gly Val Phe Gln His
                100                 105                 110
His Gln Tyr Leu Ser Pro Leu Glu Arg Lys Arg Leu Ala Arg Glu Met
            115                 120                 125
Gln Leu Ser Glu Val Gln Ile Lys Thr Trp Phe Gln Asn Arg Arg Met
        130                 135                 140
Lys His Lys Arg Gln Met Gln Asp Pro Gln Leu His Ser Pro Phe Ser
145                 150                 155                 160
Gly Ser Leu Pro Ala Pro Pro Ala Phe Tyr Ser Pro Ser Ser Gly Leu
                165                 170                 175
Ala Asn Gly Leu Gln Leu Leu Cys Pro Trp Ala Pro Leu Ser Gly Pro
            180                 185                 190
Gln Ala Leu Met Leu Pro Pro Gly Ser Phe Trp Gly Leu Cys Gln Val
        195                 200                 205
Ala Gln Glu Ala Leu Ala Ser Val Gly Ala Ser Cys Cys Gly Gln Pro
            210                 215                 220
Leu Ala Ser His Pro Pro Thr Pro Gly Arg Pro Thr Leu Gly Pro Ala
225                 230                 235                 240
Leu Ser Thr Gly Pro Arg Gly Leu Cys Ala Met Pro Gln Thr Gly Asp
                245                 250                 255
Ala Phe

<210> SEQ ID NO 112
<211> LENGTH: 260
<212> TYPE: PRT
<213> ORGANISM: Unknown
<220> FEATURE:
<223> OTHER INFORMATION: monkey
```

```
<400> SEQUENCE: 112

Met Arg Leu Ser Ser Pro Pro Arg Gly Gln Gln Gln Pro Ser Ser
1               5                  10                  15

Phe Gly Ser Val Asp Trp Leu Ser Gln Ser Ser Cys Ser Gly Leu Thr
                20                  25                  30

Pro Ser Pro Arg Pro Ala Asp Val Ser Pro Gly Ser Leu Pro Gly Pro
            35                  40                  45

Gly Gln Ile Ser Gly Ala Arg Glu Pro Pro Gln Ala Ile Ser Ile Lys
        50                  55                  60

Glu Ala Val Arg Arg Ser Ala Leu Pro Ser Pro Gln Pro Ser Met Pro
65                  70                  75                  80

Gly Leu Ser Lys Glu Pro Asn Thr Leu Arg Gly Pro Arg Val Arg Thr
                85                  90                  95

Ala Phe Thr Thr Glu Gln Val Arg Thr Leu Glu Gly Val Phe Gln His
                100                 105                 110

His Gln Tyr Leu Ser Pro Leu Glu Arg Lys Arg Leu Ala Arg Glu Met
            115                 120                 125

Gln Leu Ser Glu Val Gln Ile Lys Thr Trp Phe Gln Asn Arg Arg Met
        130                 135                 140

Lys His Lys Arg Gln Met Gln Glu Val Pro Pro Asn Ser Pro Phe Leu
145                 150                 155                 160

Gly Ser Leu His Val Pro Pro Ala Phe His Ser Pro Ser Ser Gly Leu
                165                 170                 175

Ala Asn Gly Leu Gln Leu Leu Cys Pro Trp Ala Pro Leu Pro Gly Pro
            180                 185                 190

Gln Ala Leu Met Leu Pro Pro Gly Ser Phe Trp Gly Leu Cys Gln Val
        195                 200                 205

Glu Gln Glu Ala Leu Ala Ser Thr Gly Ala Ser Cys Cys Arg Gln Pro
        210                 215                 220

Leu Ala His His Pro Pro Thr Thr Gly Ser Gly Leu Pro Ala Pro Gly
225                 230                 235                 240

Pro Ala Leu Ser Thr Gly Pro Trp Gly Leu Cys Ala Leu Pro Glu Thr
                245                 250                 255

Gly Asp Ala Phe
            260
```